United States Patent
Wu et al.

(10) Patent No.: US 10,426,755 B2
(45) Date of Patent: Oct. 1, 2019

(54) METHODS FOR INHIBITING CANCER CELLS

(71) Applicants: Chang Gung Memorial Hospital, Chiayi, Chiayi (TW); Chang Gung University, Taoyuan (TW)

(72) Inventors: Ching-Yuan Wu, Chiayi (TW); Kuan-Der Lee, Chiayi (TW); Hong-Yo Kang, Kaohsiung (TW); Yu-Shih Lin, Chiayi (TW)

(73) Assignees: CHANG GUNG MEMORIAL HOSPITAL, CHIAYI, Chiayi (TW); CHANG GUNG UNIVERSITY, Taoyuan (TW)

( * ) Notice: Subject to any disclaimer, the term of this patent is extended or adjusted under 35 U.S.C. 154(b) by 153 days.

(21) Appl. No.: 15/201,065

(22) Filed: Jul. 1, 2016

(65) Prior Publication Data

US 2017/0000760 A1   Jan. 5, 2017

Related U.S. Application Data

(60) Provisional application No. 62/187,770, filed on Jul. 1, 2015.

(51) Int. Cl.
*A61K 31/343*   (2006.01)
*A61P 35/00*   (2006.01)

(52) U.S. Cl.
CPC ............ *A61K 31/343* (2013.01); *A61P 35/00* (2018.01)

(58) Field of Classification Search
CPC .............................. A61K 31/343; A61P 35/00
See application file for complete search history.

(56) References Cited

U.S. PATENT DOCUMENTS

| 2008/0187608 A1 | 8/2008 | Dev et al. |
| 2009/0093539 A1* | 4/2009 | Wong ................... A61K 31/343 514/468 |
| 2010/0209513 A1 | 8/2010 | Jo et al. |

FOREIGN PATENT DOCUMENTS

| CN | 1264580 A | 8/2000 |
| CN | 104173368 A | 12/2014 |

OTHER PUBLICATIONS

Zhang et al 'Two New Diterpenoids from Cell Cultures of Salvia miltiorrhiza' Chem. Pharm. Bull., 61(5), p. 576-580, 2013.*
Su et al., "Salvia miltiorrhiza: Traditional medicinal uses, chemistry, and pharmacology," Chin. J. Nat. Med. Mar. 2015;13(3):163-82. PMID: 25835361. (Year: 2015).*

* cited by examiner

*Primary Examiner* — Theodore R. West
(74) *Attorney, Agent, or Firm* — Young & Thompson

(57) ABSTRACT

The present invention provides methods for treating cancer, by administering a therapeutically effective amount of a compound of formula (I), or a pharmaceutically acceptable salt thereof. Also provided are methods for reducing cancer cell metastasis, by administering a therapeutically effective amount of a compound of formula (I) described herein or a pharmaceutically acceptable salt thereof.

10 Claims, 24 Drawing Sheets i.

j.

k.

l.

(g)

(h)

(i)

(j)

(a) DU 145 cells (b) DU 145 cells (c) PC3 cells (d) PC3 cells

METHODS FOR INHIBITING CANCER CELLS

CROSS-REFERENCE TO RELATED APPLICATIONS

This application claims the benefit of priority from U.S. Provisional Application No. 62/187,770, filed Jul. 1, 2015, the entire content of which is incorporated herein by reference.

FIELD OF THE INVENTION

The present invention relates to the use of compounds of formula (I) for inhibiting or reducing cancer cells.

BACKGROUND

Cancer is the second leading cause of death worldwide, after coronary artery disease. In the United States alone, cancer causes death of well over a half-million people each year, with some 1.4 million new cases diagnosed annually. Cancer cells are characterized by uncontrolled proliferation and the ability to invade surrounding normal tissue or distant sites by homological and/or lymphatic spread.

Despite the advances made in cancer therapy over the past few decades, such as surgery, radiotherapy, chemotherapy and targeted therapy, these therapeutic modalities are still associated with significant side effects. There is an unmet need for anti-cancer treatments with less side effects and/or for chemotherapy resistant or target therapy resistant cancers. The present invention addresses this and other needs.

SUMMARY OF THE INVENTION

Accordingly, the present invention provides methods for inhibiting or reducing cancer cells by administering to a subject in need thereof a therapeutically effective amount of a compound of formula (I), or a pharmaceutically acceptable salt thereof:

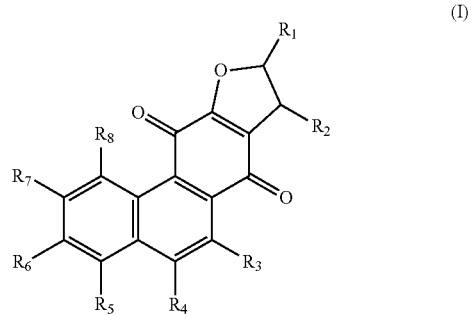

(I)

wherein $R_1$ to $R_8$ are each independently H, a deuterium, a hydroxyl group, a cyano group, a nitro group, an amino group, an amidino group, a hydrazine group, a hydrazone group, a halogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_2$-$C_{20}$ heteroaryl group, a substituted or unsubstituted monovalent non-aromatic condensed polycyclic group or a substituted or unsubstituted monovalent non-aromatic condensed heteropolycyclic group, wherein the substituent may be at least one selected from the group consisting of a deuterium, a hydroxyl group, a cyano group, a nitro group, an amino group, an amidino group, a hydrazine group, a hydrazone group, a halogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_2$-$C_{20}$ heteroaryl group, a substituted or unsubstituted monovalent non-aromatic condensed polycyclic group or a substituted or unsubstituted monovalent non-aromatic condensed heteropolycyclic group.

In one exemplary embodiment, $R_2$ and $R_5$ are each a substituted or unsubstituted $C_1$-$C_{10}$ alkyl group, and $R_1$, $R_3$, $R_4$, $R_6$, $R_7$, and $R_8$ are each H.

In another exemplary embodiment, $R_2$ and $R_5$ are each a methyl group, and $R_1$, $R_3$, $R_4$, $R_6$, $R_7$, and $R_8$ are each H.

Another aspect of the invention provides methods for reducing cancer metastasis, by administering an effective amount of compound of formula (I) described herein or a pharmaceutically acceptable salt thereof.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following Figures.

FIGS. 9h-9l are bar graphs illustrating DT reduced skps and its downstream genes, MMP2 and MMP9, in hormone therapy-resistant PC3 prostate cancer cells (Panel h), DU145 prostate cancer cells (Panels i-j) and 22RV1 prostate cancer cells (Panels k-l).

DETAILED DESCRIPTION OF THE INVENTION

Figure 1:
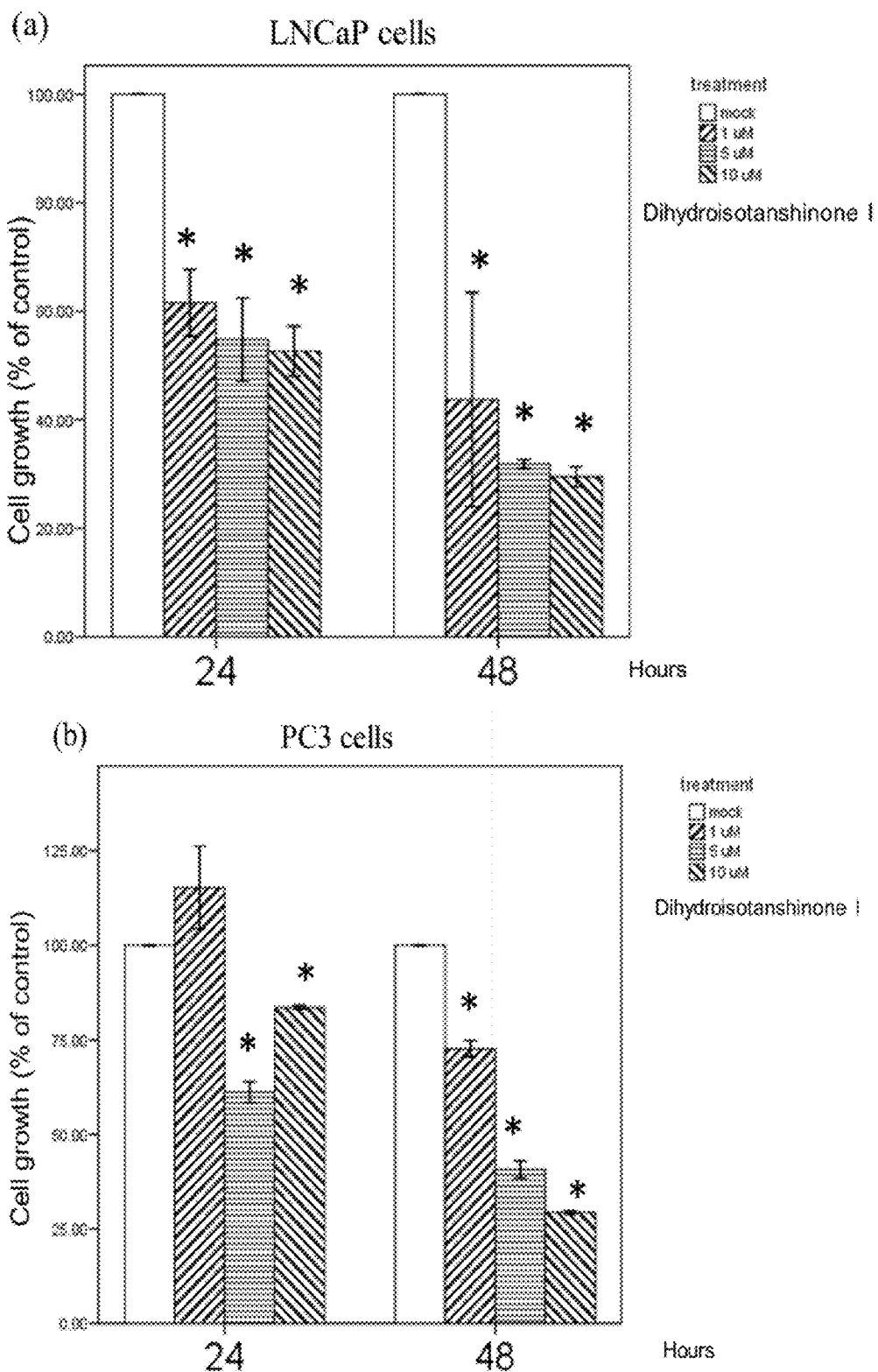
FIG. 1 is an assembly of bar graphs illustrating the effect of 1, 5 and 10 μM of an embodiment of the compounds of formula (I) (dihydroisotanshinone I or DT) in prostate cancer cell lines (LNCaP, hormone therapy-resistant PC3, DU145 and 22RV1). * Represents a statistically significant difference from the control (p<0.05).
Figure 1:
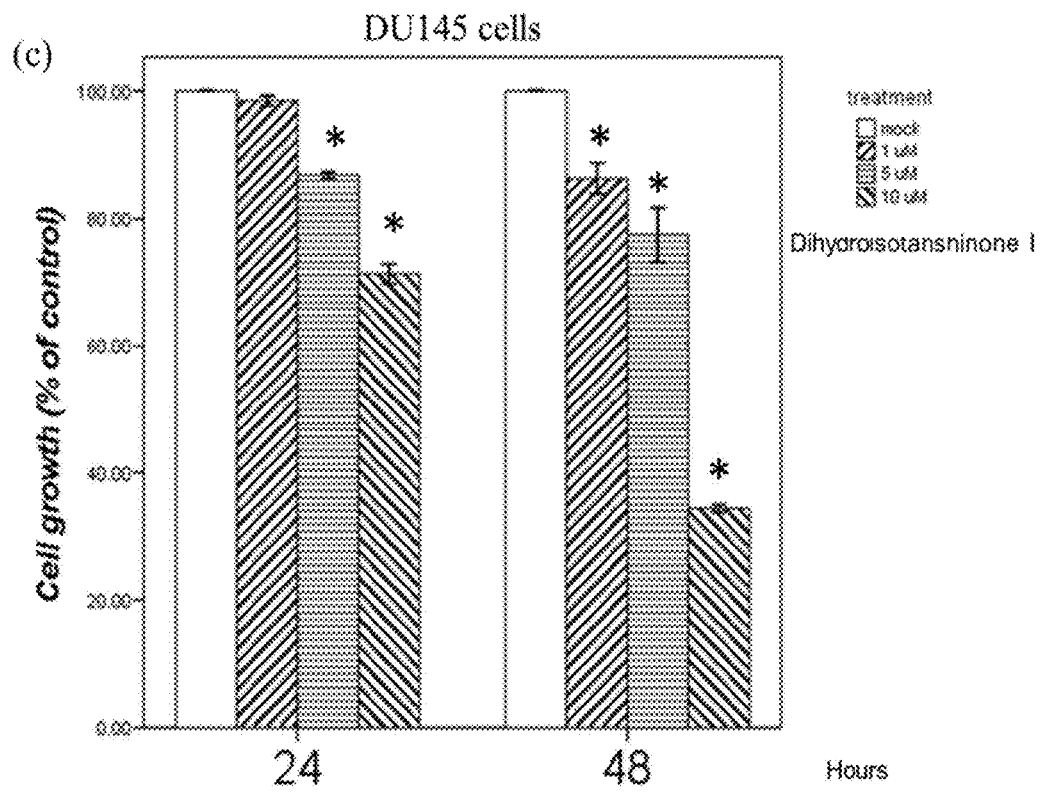
Figure 1:
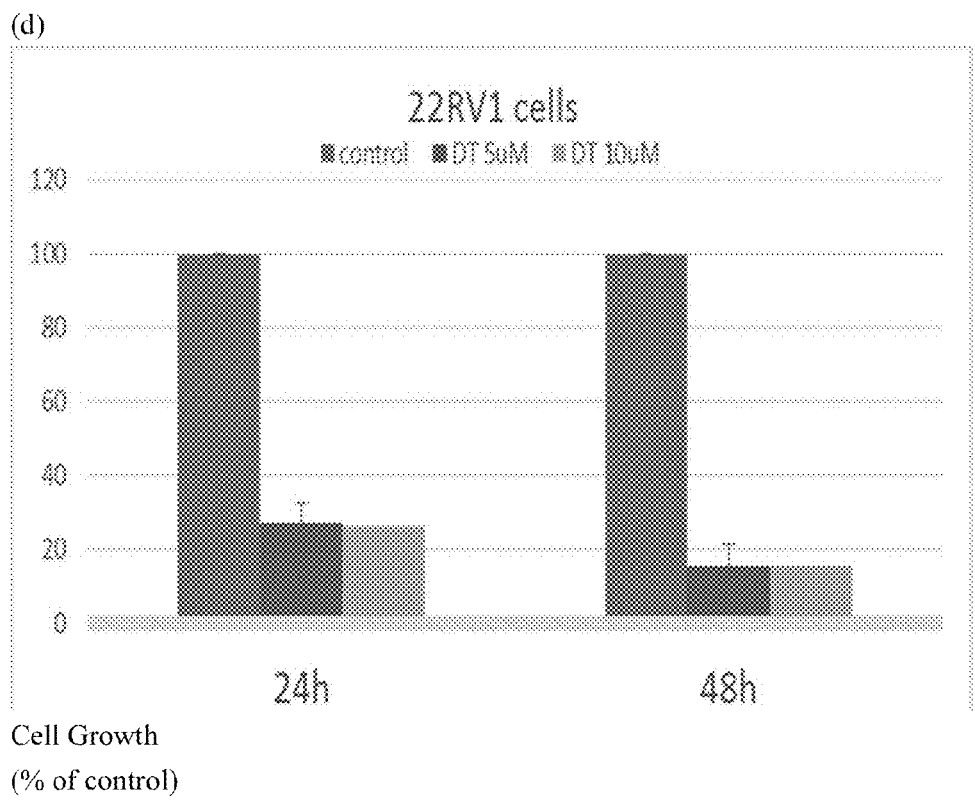

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of a compound of formula (I) that is sufficient to reduce the symptoms and/or signs of cancer, which include, but are not limited to, weight loss, pain and tumor mass, which is detectable, either clinically as a palpable mass or radiologically through various imaging means.

The term "treating," "treated," or "treatment" as used herein includes preventative (e.g. prophylactic), palliative, and curative uses or results.

The term "inhibiting" and "reducing" includes slowing, preventing or stopping the growth of.

The term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

As used herein, a cancer cell that is "resistant" to therapy is one that is unresponsive or becomes unresponsive or exhibits decreased sensitivity to therapy. In one embodiment, the cancer may be resistant at the beginning of treatment or it may become resistant during treatment.

Recitation of ranges of values herein are merely intended to serve as a shorthand method of referring individually to each separate value falling within the range, unless otherwise indicated herein, and each separate value is incorporated into the specification as if it were individually recited herein.

All numbers herein may be understood as modified by "about."

Methods for Inhibiting Cancer Cells

One aspect of the present invention is directed to methods for inhibiting or reducing cancer cells comprising administering an effective amount of the compound of formula (I) or a pharmaceutically acceptable salt thereof to a subject in need thereof, wherein the symptom or sign of cancer is reduced.

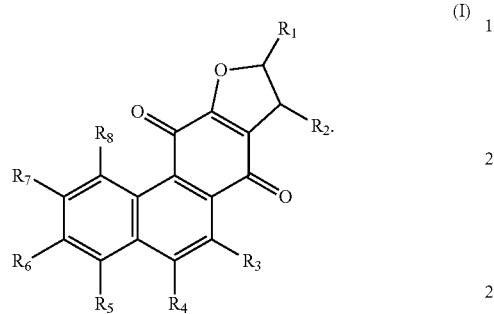

In one embodiment, $R_1$ to $R_8$ are each independently H, a deuterium, a hydroxyl group, a cyano group, a nitro group, an amino group, an amidino group, a hydrazine group, a hydrazone group, a halogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_2$-$C_{20}$ heteroaryl group, a substituted or unsubstituted monovalent non-aromatic condensed polycyclic group or a substituted or unsubstituted monovalent non-aromatic condensed heteropolycyclic group, wherein the substituent may be at least one selected from the group consisting of a deuterium, a hydroxyl group, a cyano group, a nitro group, an amino group, an amidino group, a hydrazine group, a hydrazone group, a halogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_2$-$C_{20}$ heteroaryl group, a substituted or unsubstituted monovalent non-aromatic condensed polycyclic group or a substituted or unsubstituted monovalent non-aromatic condensed heteropolycyclic group.

In another embodiment, $R_2$ and $R_5$ are each a substituted or unsubstituted $C_1$-$C_{10}$ alkyl group, and $R_1$, $R_3$, $R_4$, $R_6$, $R_7$, and $R_8$ are each H.

In yet another embodiment, $R_2$ and $R_5$ are each a methyl group, and $R_1$, $R_3$, $R_4$, $R_6$, $R_7$, and $R_8$ are each H. The compound is known as dihydroisotanshinone I or DT and the structure is depicted below.

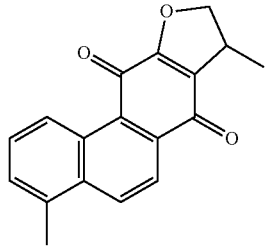 [SMILES: Cc1cccc2c3c(ccc12)C(=O)C1=C(OCC1C)C3=O]

The present invention also provides methods for reducing cancer metastasis, by administering a therapeutic effective amount of compounds of formula (I) described herein or a pharmaceutically acceptable salt thereof.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-10}$ alkyl" is intended to encompass, $C_1$, $C_2$, $C_3$, $C_4$, $C_5$, $C_6$, $C_7$, $C_8$, $C_9$, $C_{10}$, $C_{1-6}$, $C_{1-10}$, $C_{1-9}$, $C_{1-8}$, $C_{1-7}$, $C_{1-6}$, $C_{1-5}$, $C_{1-4}$, $C_{1-3}$, $C_{2-10}$, $C_{2-10}$, $C_{3-10}$, $C_{4-10}$, $C_{5-10}$, $C_{6-10}$, $C_{7-10}$, $C_{2-9}$, $C_{4-5}$, and $C_{5-6}$ alkyl.

"$C_{1-10}$ alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —CH$_3$). In certain embodiments, the alkyl group is a substituted $C_{1-10}$ alkyl.

A $C_1$-$C_{10}$ alkoxy group as used herein refers to a monovalent group represented by —OA$_1$ (where A$_1$ is the $C_1$-$C_{10}$ alkyl group), and non-limiting examples thereof include a methoxy group, an ethoxy group, and an isopropyloxy group.

As used herein, "$C_2$-$C_{10}$ alkenyl" refers to a radical of a straight-chain or branched hydrocarbon group having from 2 to 10 carbon atoms and one or more double bonds (e.g., 1, 2, 3, or 4 double bonds). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_2$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ("allyl", $C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "$C_2$-$C_{10}$ alkynyl" refers to a radical of a straight-chain or branched hydrocarbon group having from 2 to 10 carbon atoms and one or more triple bonds (e.g., 1, 2, 3, or 4 triple bonds) ("$C_{2-10}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_2$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

A $C_3$-$C_{10}$ cycloalkyl group as used herein refers to a monovalent hydrocarbon monocyclic group having 3 to 10 carbon atoms as ring-forming atoms, and non-limiting examples thereof include a cyclopropyl group, a cyclobutyl group, a cyclopentyl group, a cyclohexyl group, and a cycloheptyl group.

A $C_2$-$C_{10}$ heterocycloalkyl group as used herein refers to a monovalent monocyclic group having at least one hetero atom selected from N, O, P, and S as a ring-forming atom and 1 to 10 carbon atoms as the remaining ring-forming atoms, and non-limiting examples thereof include a tetrahydrofuranyl group and a tetrahydrothienyl group.

A $C_3$-$C_{10}$ cycloalkenyl group as used herein refers to a monovalent monocyclic group that has 3 to 10 carbon atoms as ring-forming atoms and at least one carbon-carbon double bond in the ring thereof, and does not have overall aromaticity. Non-limiting examples of the $C_3$-$C_{10}$ cycloalkenyl group include a cyclopentenyl group, a cyclohexenyl group, and a cycloheptenyl group.

A $C_2$-$C_{10}$ heterocycloalkenyl group as used herein refers to a monovalent monocyclic group that has at least one hetero atom selected from N, O, P, and S as a ring-forming atom, 1 to 10 carbon atoms as the remaining ring-forming atoms, and at least one double bond in its ring. Non-limiting examples of the $C_1$-$C_{10}$ heterocycloalkenyl group include a 2,3-dihydrofuranyl group and a 2,3-dihydrothienyl group.

A $C_6$-$C_{20}$ aryl group as used herein refers to a monovalent group having a carbocyclic aromatic system including 6 to 20 carbon atoms, and a $C_6$-$C_{20}$ arylene group as used herein refers to a divalent group having a carbocyclic aromatic system having 6 to 20 carbon atoms. Non-limiting examples of the $C_6$-$C_{20}$ aryl group include a phenyl group, a naphthyl group, an anthracenyl group, a phenanthrenyl group, a pyrenyl group, and a chrysenyl group.

A $C_2$-$C_{20}$ heteroaryl group as used herein refers to a monovalent group having a carbocyclic aromatic system that has at least one hetero atom selected from N, O, P, and S as a ring-forming atom, and 2 to 20 carbon atoms. Non-limiting examples of the $C_2$-$C_{20}$ heteroaryl group include a pyridinyl group, a pyrimidinyl group, a pyrazinyl group, a pyridazinyl group, a triazinyl group, a quinolinyl group, and an isoquinolinyl group.

A $C_6$-$C_{20}$ aryloxy group as used herein refers to a group represented by —$OA_2$ (where $A_2$ is the $C_6$-$C_{20}$ aryl group), and a $C_6$-$C_{20}$ arylthio group refers to a group represented by —$SA_3$ (where $A_3$ is the $C_6$-$C_{20}$ aryl group).

A monovalent non-aromatic condensed polycyclic group as used herein refers to a cyclic monovalent group (for example, having 8 to 20 carbon atoms) that includes two or more rings condensed to each other, only carbon atoms as ring forming atoms, and the entire molecular structure does not have overall aromaticity. Non-limiting example of the monovalent non-aromatic condensed polycyclic group is a fluorenyl group.

A monovalent non-aromatic condensed heteropolycyclic group as used herein refers to a cyclic monovalent group (for example, having 2 to 20 carbon atoms) that includes two or more rings condensed to each other, has at least one heteroatom selected from N, O, P, and S as a ring forming atom, and carbon atoms as the remaining ring-forming atoms, and the entire molecular structure does not have overall aromaticity. Non-limiting example of the monovalent non-aromatic condensed heteropolycyclic group is a carbazolyl group.

Pharmaceutically acceptable salts of the compounds of formula (I) and physiologically functional derivatives thereof include salts derived from an appropriate base, such as an alkali metal (for example, sodium, potassium), an alkaline earth metal (for example, calcium, magnesium), ammonium and $NY_4^+$ (wherein Y is $C_1$-$C_4$ alkyl). Pharmaceutically acceptable salts of an amino group include salts of organic carboxylic acids, such as tartaric, aliphatic, cycloaliphatic, aromatic, heterocyclic, carboxylic and sulfonic classes of organic acids, such as, for example, formic, glucuronic, malic, maleic, fumaric, pyruvic, aspartic, glutamic, benzoic, anthranilic, mesylic, salicylic, hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, hydroxybutyric, cyclochexylaminosulfonic, galactaric and galacturonic acid and the like, lactobionic, fumaric, and succinic acids; organic sulfonic acids, such as methaniesulfolic, ethanesulfonic, isothionic, benzenylesulfonic and p-toluenesulfonic acids; and inorganic acids such as hydrochloric, hydrobromic, hydroiodic, nitric, carbonic, sulfuric, sulfamic and phosphoric acid and the like. Pharmaceutically acceptable salts of a compound having a hydroxy group consist of the anion of said compound in combination with a suitable cation such as $Na^+$, $NH_4^+$ or $NX_4^+$ (wherein X is, for example, a $C_1$-$C_4$ alkyl group), $Ca^{++}$, $Li^+$, $Mg^{++}$, or, $K^+$ and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound in free form.

In one embodiment, the compound of formula (I) or a pharmaceutically acceptable salt thereof can be administered alone. In another embodiment, the compound of formula (I) or a pharmaceutically acceptable salt thereof can be administered in combination with a pharmaceutically acceptable carrier or excipient, as a pharmaceutical composition.

A "pharmaceutically acceptable carrier" refers to a carrier that, after administration to or upon a subject, does not cause undesirable physiological effects. The carrier in a pharmaceutical composition must be "acceptable" also in the sense that is compatible with the active compound and, preferably, capable of stabilizing it. Suitable pharmaceutically acceptable carriers are well known in the art and vary with the desired form and mode of administration of the pharmaceutical composition. For example, they may include, but are not limited to, biocompatible vehicles, adjuvants, additives (such as pH-adjusting additives), diluents or excipients such as fillers, binders, wetting agents, disintegrators, surface-active agents, lubricants and the like. The excipients may be nonionic surfactants, polyvinylpyrollidone, human serum albumin, aluminum hydroxide, agents with anesthetic action, and various unmodified and derivatized cyclodextrins. More preferably, the nonionic surfactants may include Polysorbate 20, Polysorbate 40, Polysorbate 60, and Polysorbate 80. The polyvinylpyrollidone may preferably be Plasdone C15, a pharmaceutical grade of polyvinylpyrollidone. The agent having anesthetic action preferably is benzyl alcohol. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers. One or more pharmaceutical carriers may be used for the delivery of a compound of formula (I).

The pharmaceutical composition can be prepared by any method known in the art of pharmacy. Such methods include the step of bringing into association the active compound with one or more carriers. For instance, to prepare compositions suitable for injection, solutions and suspensions are sterilized and are preferably isotonic to blood. In making injectable preparations, carriers which are commonly used in this field are used, for example, water, ethyl alcohol, propylene glycol. In these instances, adequate amounts of isotonicity adjusters such as sodium chloride, glucose or glycerin can be added to make the preparations isotonic. The aqueous sterile injection solution may further comprise oxidants, buffers, and other similar additions, which are acceptable for parenteral compositions.

For instance, for oral administration in the form of a tablet or capsule, the active compound can be comminuted with a pharmaceutically acceptable carrier such as ethanol, glycerol, water and the like. Powders are prepared by comminuting the compound to a suitable fine size and mixing it with a comminuted pharmaceutical carrier such as an edible carbohydrate, for example, starch or mannitol. Flavoring, dispersing and coloring agents can also be present.

For the treatment of the eyes or other external tissues, for example, the mouth and the skin, the pharmaceutical compositions are preferably applied as a topical ointment or cream. When formulated in an ointment, the active compound may be employed with either a paraffinic or a water-miscible ointment base. Alternatively, the active compound may be formulated in a cream with an oil-in-water cream base or a water-in-oil base.

The term "administering" covers inhalation, topical, oral, rectal, implanted reservoir and parenteral (such as intravenous, intramuscular, subcutaneous, intra-articular, intra-synovial, cisternal, intrathecal, intrahepatic, intralesional and intracranial) delivery to a subject the active compound of the invention. Parenteral and oral routes of administration are preferred.

The composition for oral administration can be any orally acceptable dosage form including capsules, tablets, emulsions and aqueous suspensions, dispersions, and solutions.

The oral composition may include sustained release properties as well as rapid delivery forms.

The compounds of formula (I), the pharmaceutically acceptable salt thereof or the pharmaceutical compositions described herein can be administered in a single dose treatment or in multiple dose treatments on a schedule and over a time period appropriate to the age, weight and condition of the subject, the particular composition used, and the route of administration, whether the pharmaceutical composition is used for prophylactic or curative purposes, etc. For example, in one embodiment, the pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of the compounds of formula (I), the pharmaceutically acceptable salt thereof or the pharmaceutical compositions described herein, e.g., the period of time over which the compound or the pharmaceutical composition is administered, can vary, depending on any of a variety of factors, e.g., subject response, etc. For example, the compound, or the pharmaceutical composition can be administered over a period of time ranging from about one or more seconds to one or more hours, one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

For ease of administration and uniformity of dosage, oral or parenteral pharmaceutical compositions in dosage unit form may be used. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The compounds of formula (I) and methods can be used to treat any type of cancer. In one embodiment, the cancer is not cervical cancer. In one embodiment, the cancer cells are selected from prostate cancer, endometrial cancer, lung cancer, breast cancer and colorectal cancer. In another embodiment, the cancer cells are therapy resistant. Non limiting examples of therapy resistant cancer cells are breast cancer, colorectal cancer, lung cancer and prostate cancer. In one exemplary embodiment, the cancer cells are chemotherapy resistant. In another exemplary embodiment, the cancer cells are target therapy resistant. In some embodiments, target therapy are medications which inhibit the growth of cancer cells by interfering with specific targeted molecules needed for carcinogenesis and cancer growth. Non limiting examples of target therapy include tamoxifen for breast cancer and hormone therapy for prostate cancer.

The compounds of formula (I) can also be used to treat metastatic cancer. Non limiting examples of metastatic cancer are prostate cancer and lung cancer.

Treatment may be administered alone, or as an adjuvant to surgery, chemotherapy or radiotherapy, e.g., before surgery to reduce the tumor size and/or following radiotherapy to reduce the possibility of metastases.

The data obtained from the cell culture assays and animal studies can be used in formulating a range of dosage for use in humans. In one embodiment, the dosage of such compounds lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

The following examples further illustrate the present invention. These examples are intended merely to be illustrative of the present invention and are not to be construed as being limiting.

Example 1: The Effect of DT on the Proliferation of Prostate Cancer Cells

An in vitro evaluation of the effect of dihydroisotanshinone I (DT) on the following prostate cancer cell lines was performed: LNCaP (with lymph node metastasis), hormone therapy resistant PC3 (with bone metastasis), 22RV1, DU145 (with brain metastasis), were obtained from Bioresource Collection and Research Center, Taiwan and DT was purchased from ChemFaces Co., Ltd., China.

The prostate cancer cells were plated at a density of $10^3$ or $3 \times 10^3$ per well, in a 96-well plate, in a medium containing 10% Fetal bovine serum (FBS) (Gibco®, commercially available from Life Technologies, USA). Once the prostate cancer cells were attached to the culture dish, the 10% FBS medium was replaced with a second 10% FBS medium and each of the prostate cancer cell line was treated with 1, 5, and 10 µM of DT respectively for 1-2 days. The absorbance was measured using XTT assay kit (commercially available from Roche, Switzerland) at 492 nm using an ELISA reader (Bio-Rad Laboratories, USA).

Results: Panels (a)-(d) of FIG. 1 show that DT inhibits prostate cancer cell proliferation in a dose dependent fashion.

Example 2: The Effect of DT on the Proliferation of Lung Cancer Cells

An in vitro evaluation of the effect of DT, gemcitabine (a chemotherapeutic agent) and etoposide (a chemotherapeutic agent) on the lung cancer cells was performed. The lung cancer cell lines, chemotherapy-resistant/metastatic H460 lung cancer cells (with pleural metastasis) and A549 lung cancer cells, were purchased from Bioresource Collection and Research Center, Taiwan. The lung cancer cells were plated according to the steps in Example 1 and each of the lung cancer cell line was treated with 5, 10 and 20 µM of DT, 10 and 20 µM of Gemcitabine hydrochloride and 10 and 20 µM of etoposide respectively for 1-2 days. The absorbance was measured using XTT assay kit at 492 nm using an ELISA reader.

Figure 2:
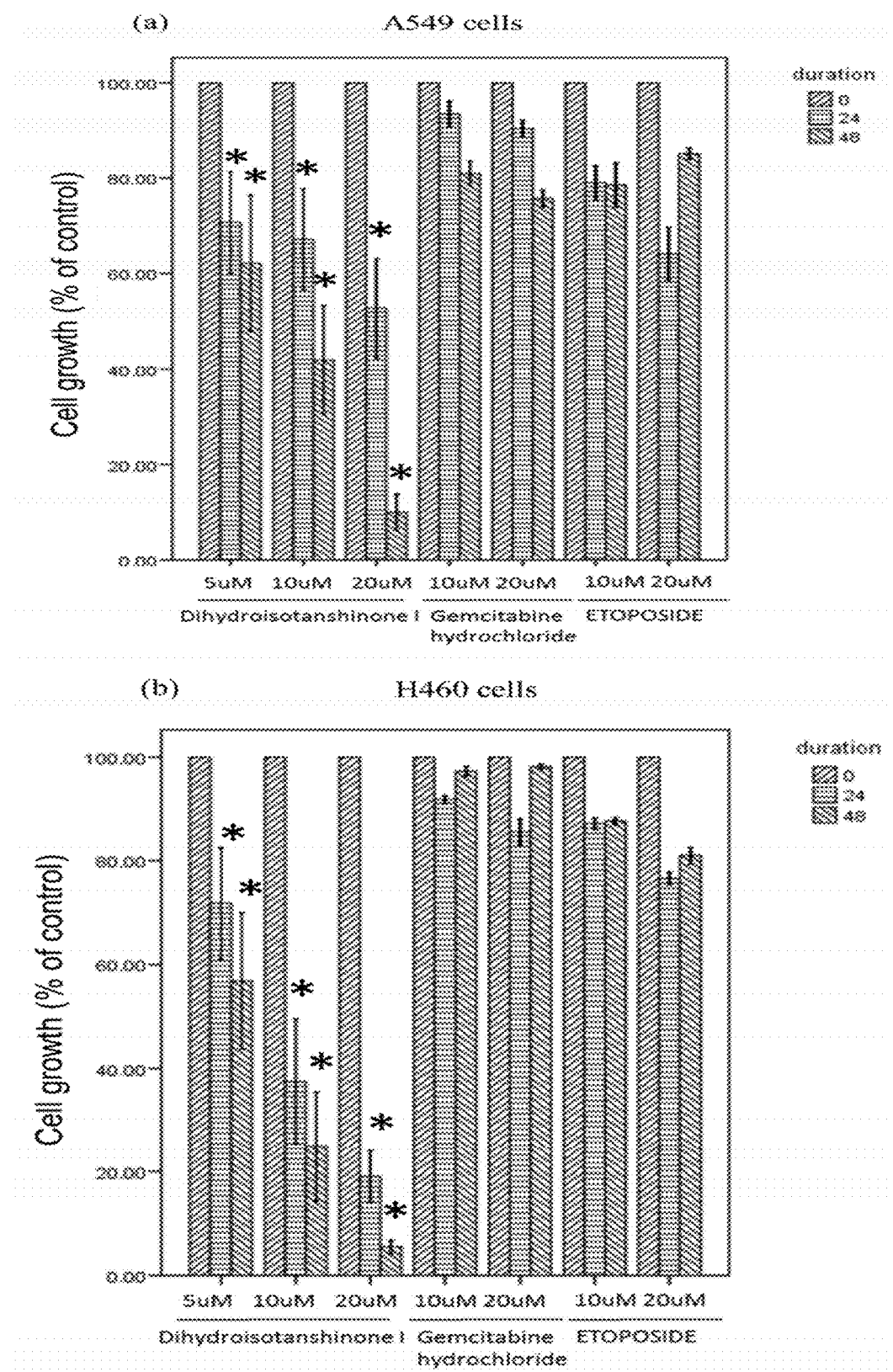
FIG. 2 illustrates the suppressive effect of one embodiment of the compounds of formula (I) (DT), gemcitabine and etoposide on lung cancer cell lines (Panel (a) for A549 lung cancer cell line and Panel (b) for chemotherapy-resistant/metastatic H460 lung cancer cell line).

Results: FIG. 2 shows that regardless of the dosage, DT is more effective than gemcitabine and etoposide in inhibiting lung cancer proliferation, even for the chemotherapy resistant/metastatic H460 lung cancer cells. DT inhibits the lung cancer cells in a dose dependent fashion.

Example 3: The Effect of DT on the Proliferation of Breast Cancer Cells

An in vitro evaluation of the effect of DT on the breast cancer cells was performed. The breast cancer cell lines, MDA-MB-231, MCF-7 and tamoxifen-resistant MCF-7 breast cancer cells were obtained from Bioresource Collection and Research Center, Taiwan. The breast cancer cells were cultured in Eagle's Minimum Essential Medium containing 10% charcoal-stripped fetal bovine serum and plated according to the steps in Example 1 and each of the breast cancer cell line was treated with 0 (control), 5, 10 and 20 µM of DT, respectively for 1-3 days. The absorbance was measured using XTT assay kit at 492 nm using an ELISA reader.

Figure 3:
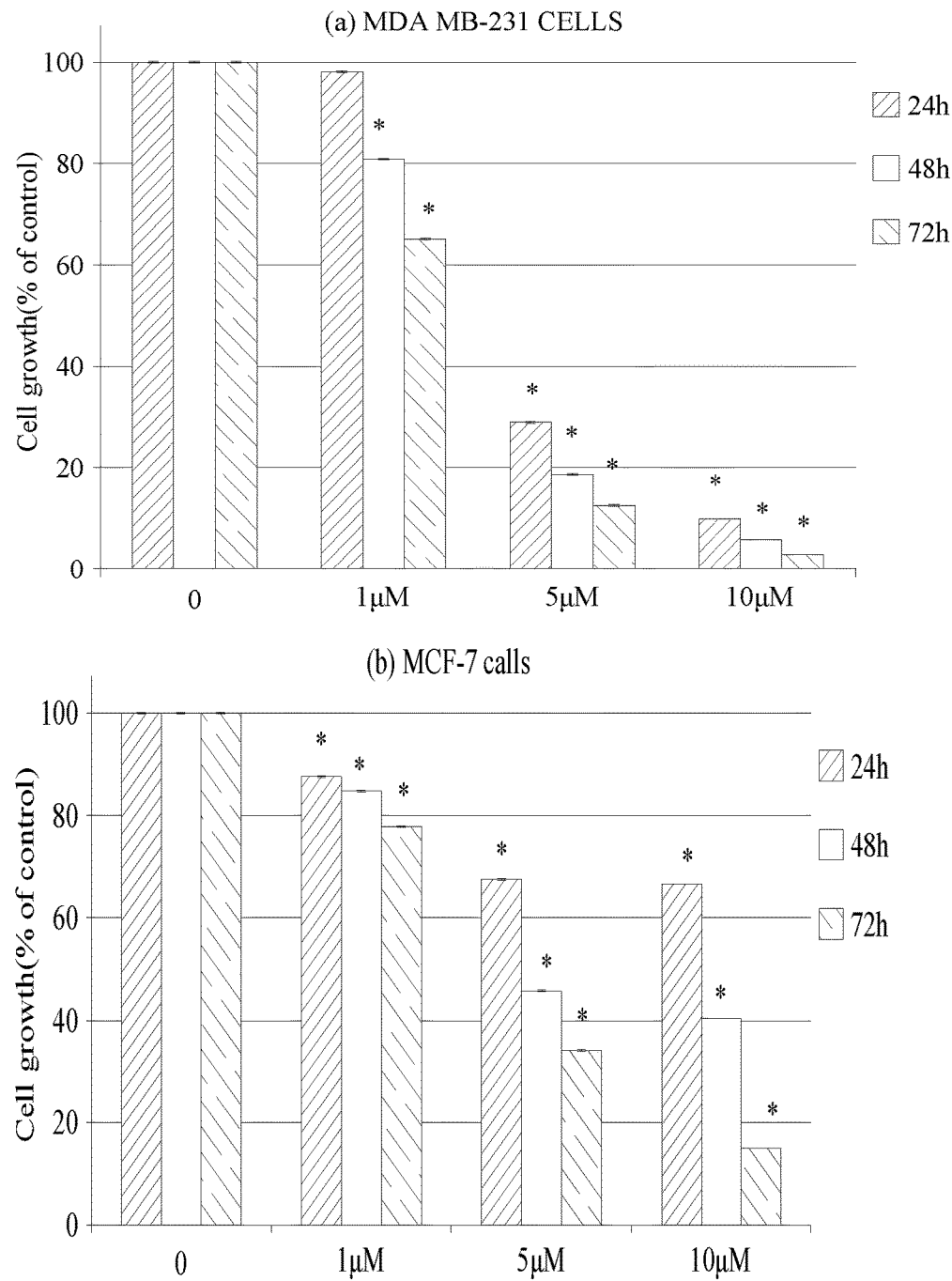
FIG. 3 is an assembly of bar graphs illustrating the effect of 1, 5 and 10 µM of an embodiment of the compounds of formula (I) (DT) on breast cancer cells lines (Panel (a) for MDA MB-231, Panel (b) for MCF-7 and Panel (c) for tamoxifen-resistant MCF-7).
Figure 3:
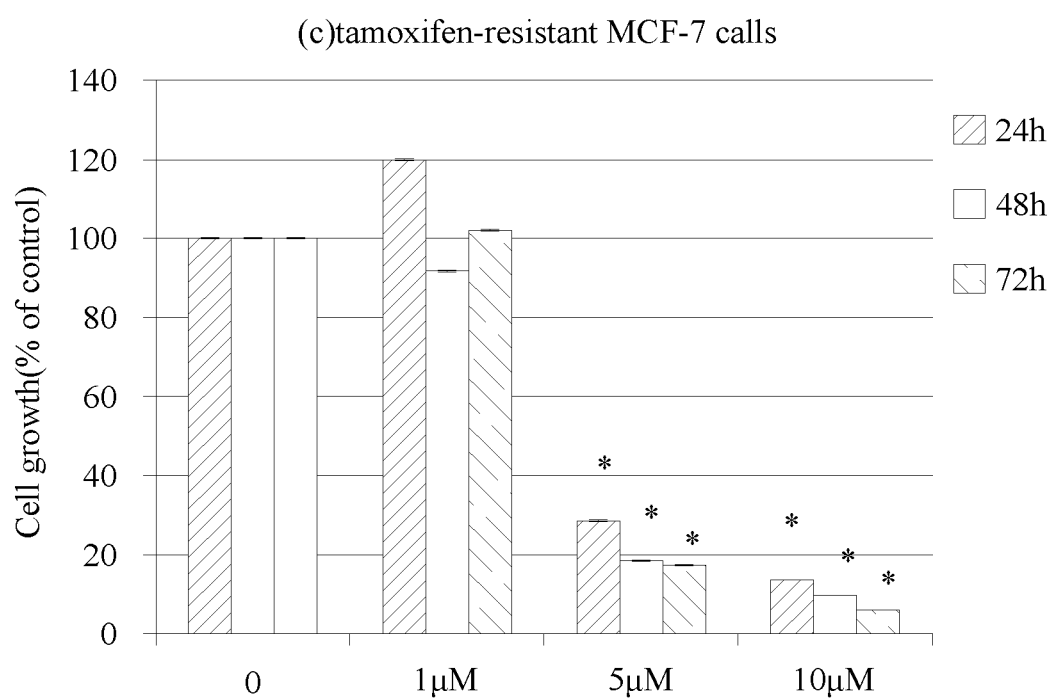

Results: FIG. 3 shows that DT is effective in inhibiting breast cancer cells, even for the tamoxifen-resistant MCF-7 breast cancer cells, in a dose dependent and time dependent fashion. A higher dose of DT is required (>1 µM) is required for inhibiting tamoxifen-resistant MCF-7 breast cancer cells (see Panel (c) of FIG. 3).

Example 4: The Effect of DT on the Proliferation of Endometrial Cancer Cells

An in vitro evaluation of the effect of DT on endometrial cancer cells was performed. The endometrial cancer cell lines, ARK1 and ARK2, were provided by Dr. T H Wang at Chang Gung Meorial Hospital, Linkou, Taiwan)

The endometrial cancer cells were cultured and plated according to the steps in Example 1 and each of the endometrial cancer cell line was treated with 0 (control), 5, 10 and 20 µM of DT, respectively for 1-2 days. The absorbance was measured using XTT assay kit at 492 nm using an ELISA reader.

Figure 4:
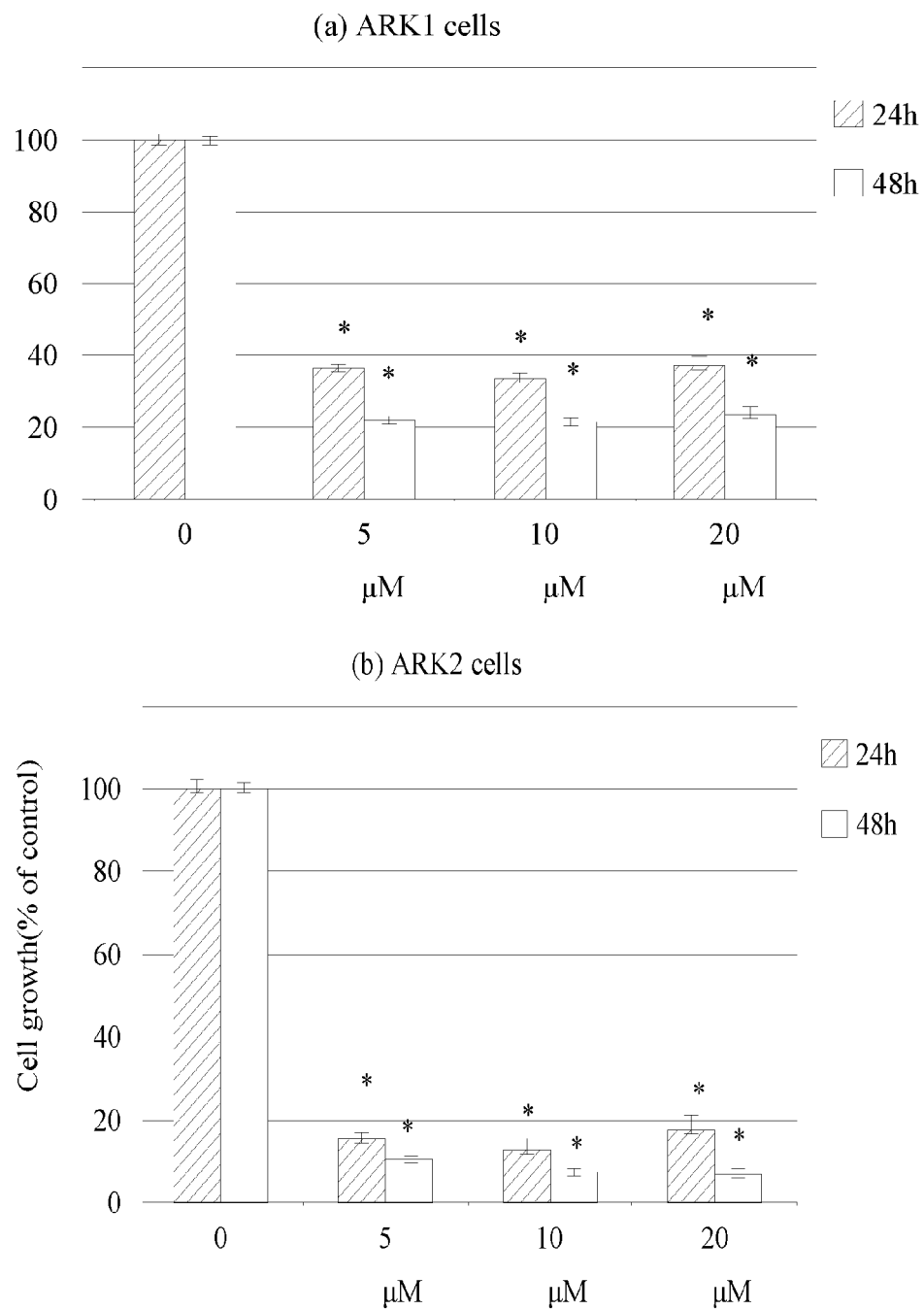
FIG. 4 are bar graphs showing the effect of 5, 10 and 20 µM of an embodiment of the compounds of formula (I) (DT) on endometrial cancer cells (ARK1 in Panel (a) and ARK2 in Panel (b)).

Results: FIG. 4 shows that DT is effective in inhibiting ARK1 and ARK2 endometrial cancer cells.

Example 5: The Effect of DT on the Proliferation of Colorectal Cancer Cells

An in vitro evaluation of the effect of DT on the chemotherapy-resistant colorectal cancer cells was performed. The chemotherapy-resistant colorectal cancer cells (HCT116) were obtained from Dr. K D Lee at Chang Gung Memorial Hospital, Chiayi, Taiwan. The colorectal cancer cells were cultured and plated according to the steps in Example 1 and treated with 0 (control), 1, 5 and 10 µM of DT, respectively for 1-3 days. The absorbance was measured using XTT assay kit at 492 nm using an ELISA reader.

Figure 5:
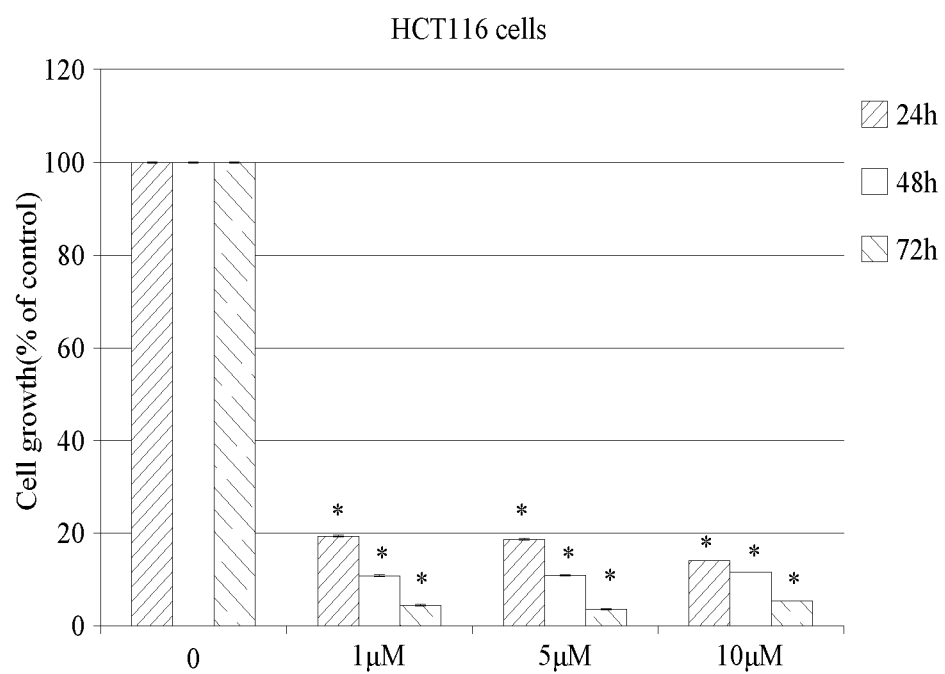
FIG. 5 is a bar graph illustrating the effect of 1, 5 and 10 µM of an embodiment of the compounds of formula (I) (DT) on chemotherapy-resistant colorectal cancer cells HCT-116.

Results: FIG. 5 shows that DT is effective in inhibiting chemotherapy-resistant colorectal cancer cells in a dose dependent manner.

Example 6: The Effect of DT on Cancer Cells Apoptosis/Necrosis

The effect of DT on metastatic prostate cancer cells (hormone therapy-resistant PC3, DU145 and LNCaP); lung cancer cells (A549 and chemotherapy-resistant/metastatic H460); and breast cancer cells (MCF-7, tamoxifen-resistant MCF7 and MDA MB-231) was assessed.

$1 \times 10^6$ Cancer cells were seeded in a 100-mm plate and cultured overnight. The cancer cells were treated with phosphate buffered saline (PBS), a Dimethyl sulfoxide (DMSO) vehicle (CT), 10 or 20 µM of DT for 24-48 hours, then collected and washed with cold PBS. The supernatant was removed by centrifugation and resuspended in FITC Annexin V binding buffer and Propidium iodide (PI) (Annexin V-FITC Apoptosis Detection Kit, commercially available from Strong Biotech Corporation, Taiwan). The suspended cancer cells were stained at room temperature, in the dark for 15 min and analyzed by the BD FACSCanto™ flow cytometry (Becton Dickinson, USA). The amount of early apoptosis, late apoptosis, and necrosis was measured as the percentage of annexin-V positive/PI negative (Q4 in the FACS images), annexin-V positive/PI positive (Q2 in the FACS images), and annexin-V negative/PI positive cells (Q1 in the FACS images), respectively. Normal cells are in Q2 of the FACS images.

Figure 6:
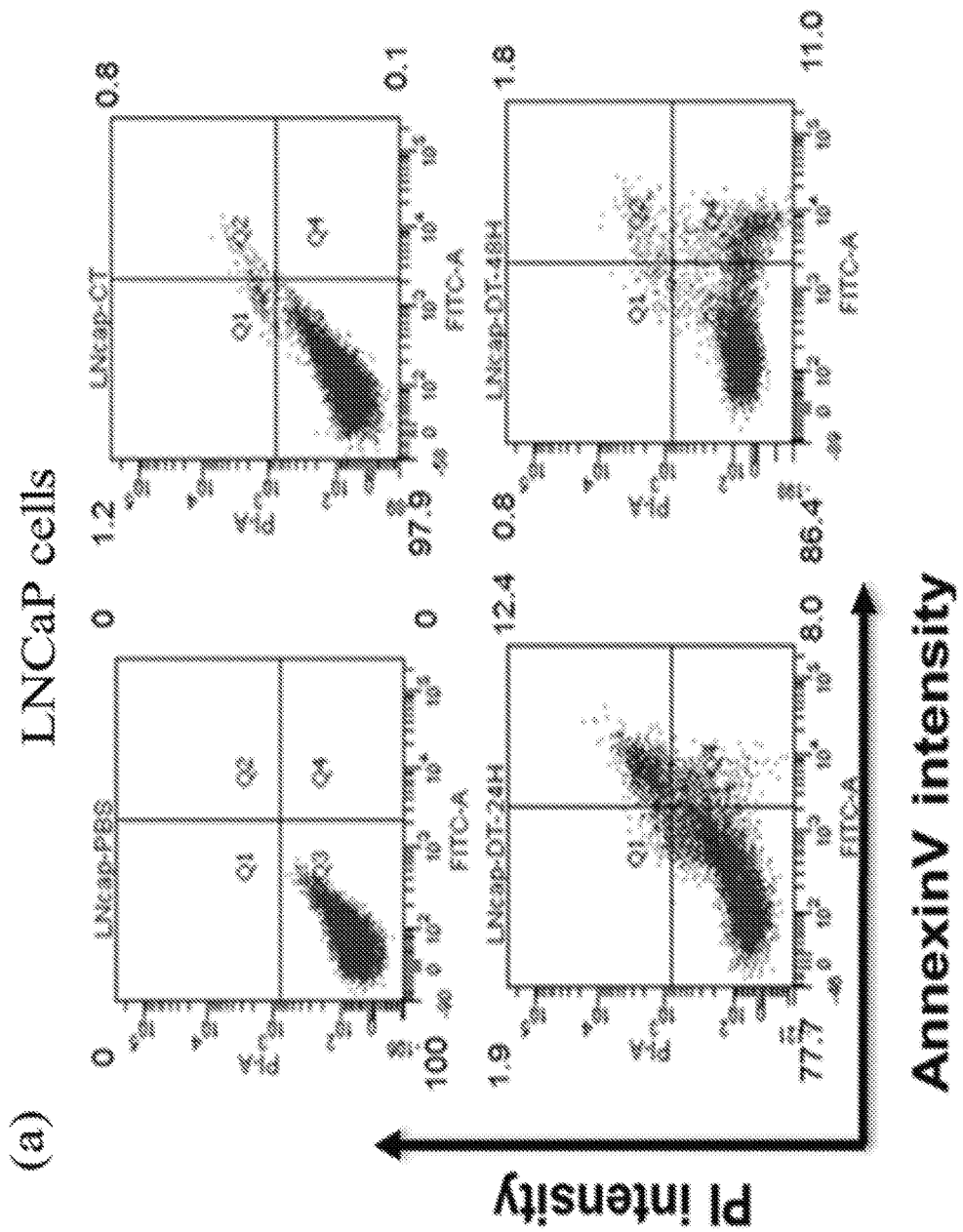
FIG. 6 is a series of flow cytometry (FACS) images, illustrating an embodiment of the compounds of formula (I) (DT) induced prostate cancer cell apoptosis/necrosis. Panels (a)-(c) show apoptosis of LNCaP prostate cancer cells, hormone therapy-resistant PC3 cancer cells and DU145 prostate cancer cells respectively, after the treatment with phosphate buffered saline (PBS), DMSO control vehicle (CT) and DT for 24-48 hours. Q1 indicates necrotic cells; Q2 indicates late apoptosis; Q3 indicates normal cells; and Q4 indicates early apoptosis.
Figure 6:
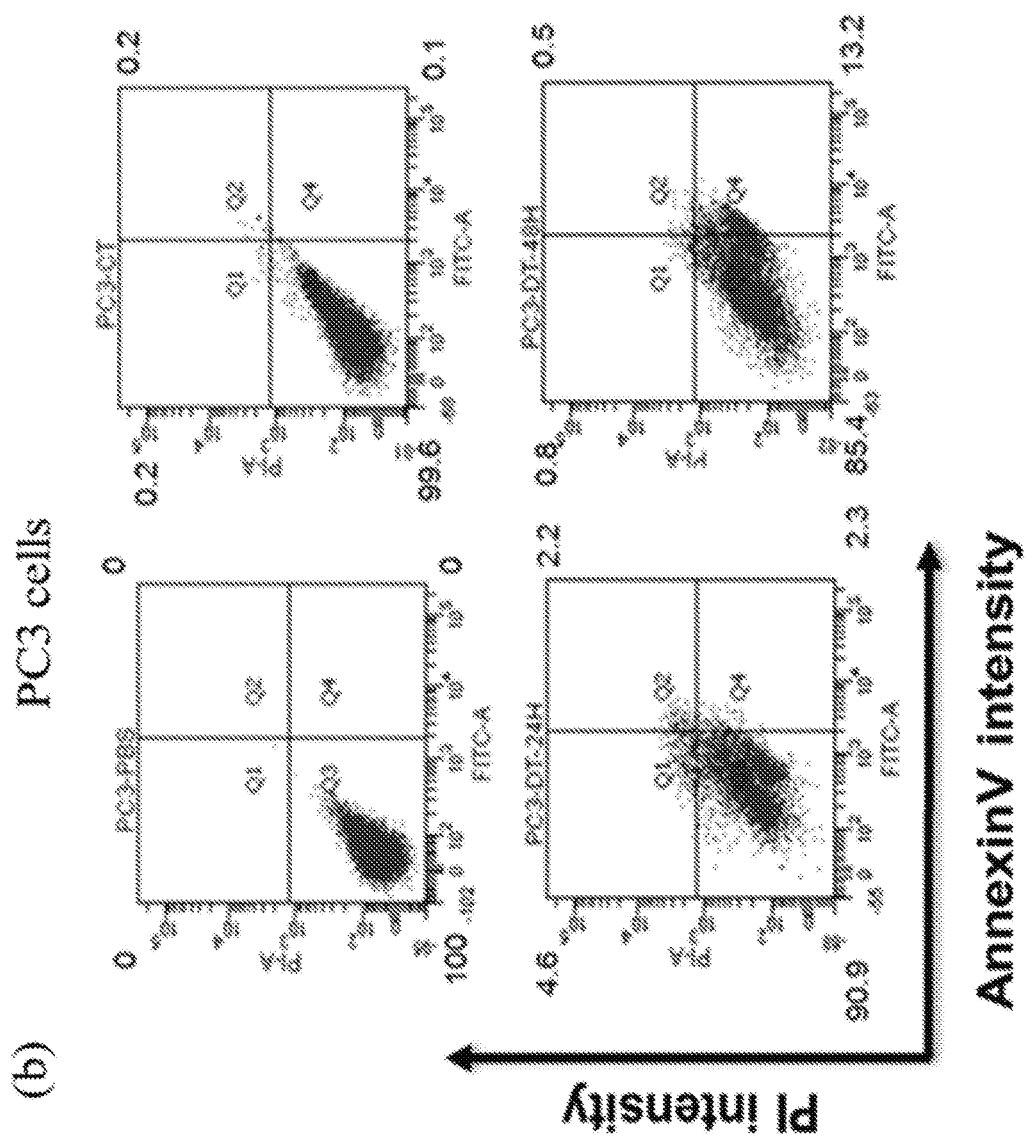
Figure 6:
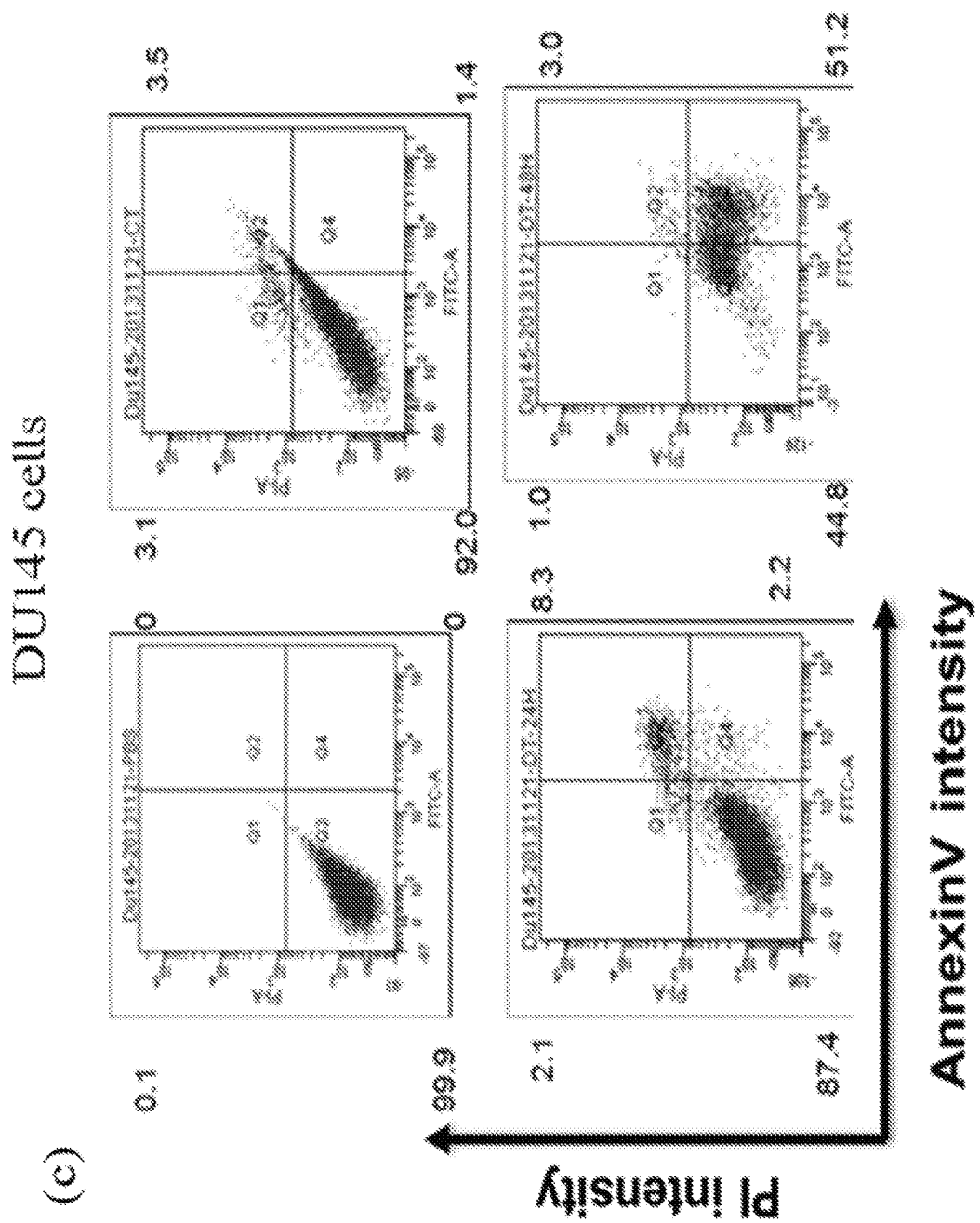
Figure 7:
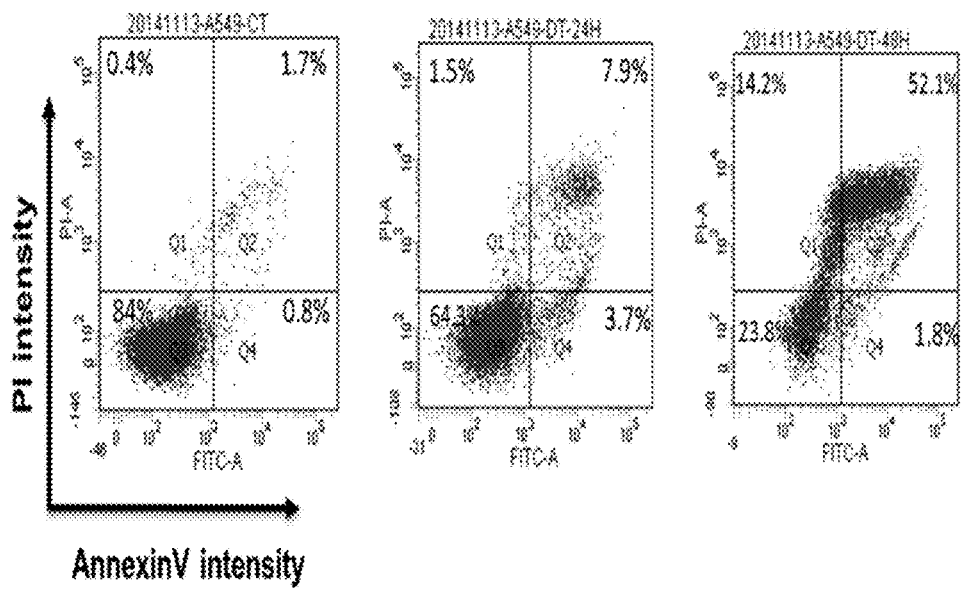
FIG. 7 is a series of FACS images, illustrating an embodiment of the compounds of formula (I) (DT) induced lung cancer cell apoptosis/necrosis. Panel (a) shows A549 cancer cell apoptosis/necrosis and Panel (b) shows chemotherapy-resistant/metastatic H460 cancer cell apoptosis/necrosis after the treatment with DMSO vehicle (CT) and DT for 24-48 hours.
Figure 7:
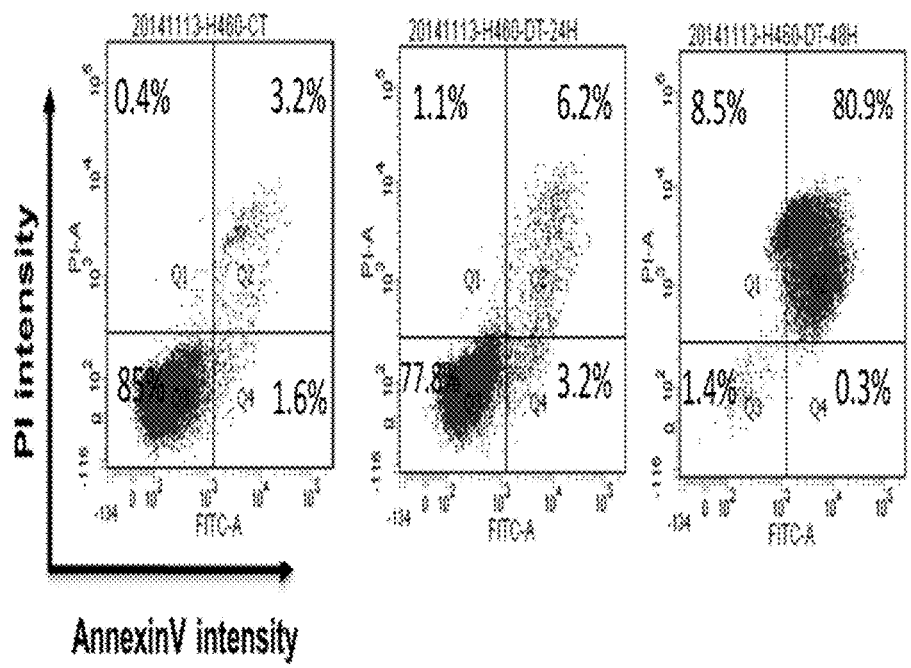
Figure 8:
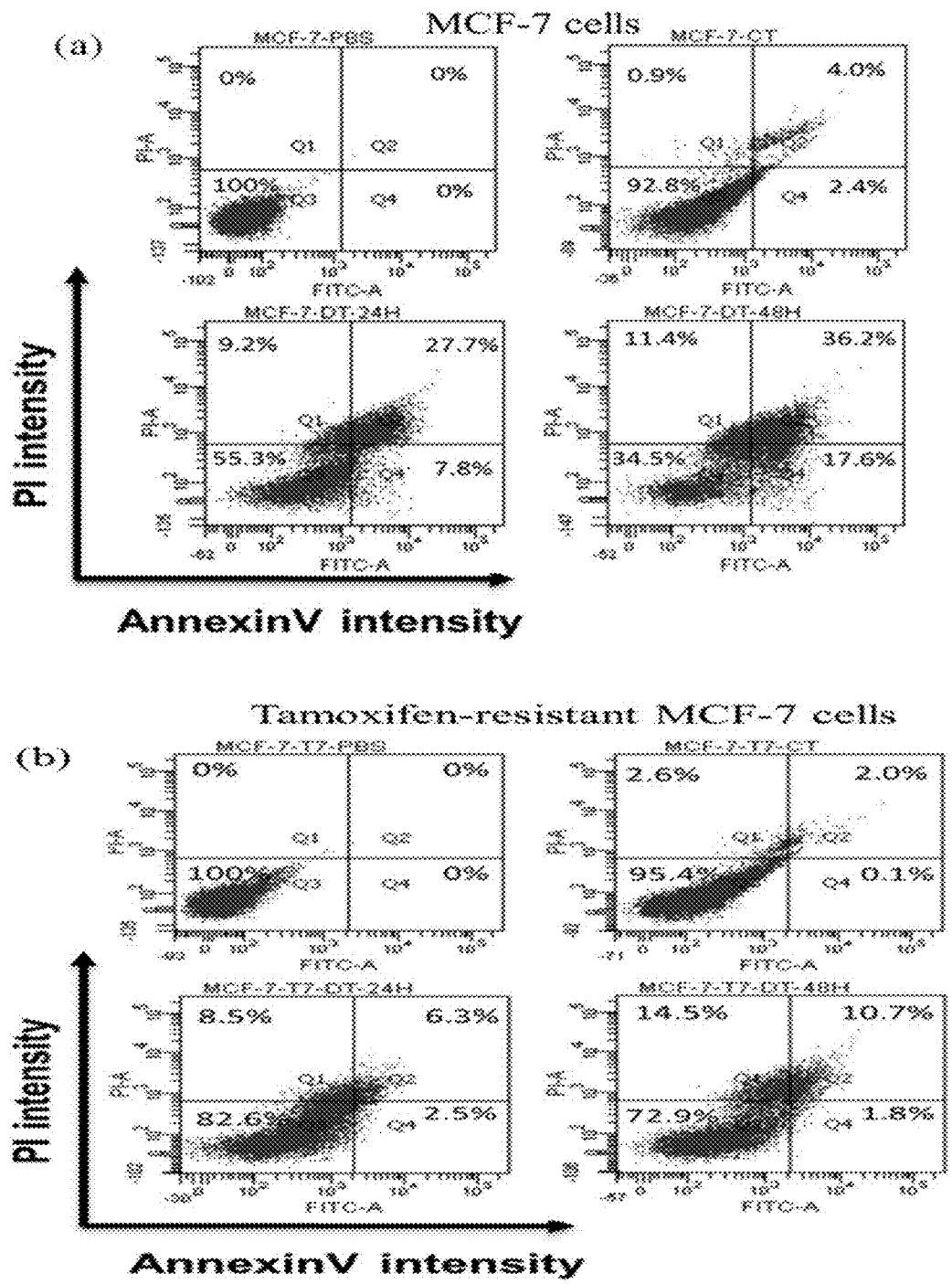
FIG. 8 is a series of FACS images, illustrating apoptosis/necrosis of breast cancer cells induced by an embodiment of the compounds of formula (I) (DT). Panels (a)-(c) show apoptosis and necrosis of MCF-7 cancer cells, tamoxifen-resistant MCF-7 cancer cells and MDA MB-231 cancer cells respectively, in the presence of PBS, a control agent, and DT for 24-48 hours.
Figure 8:
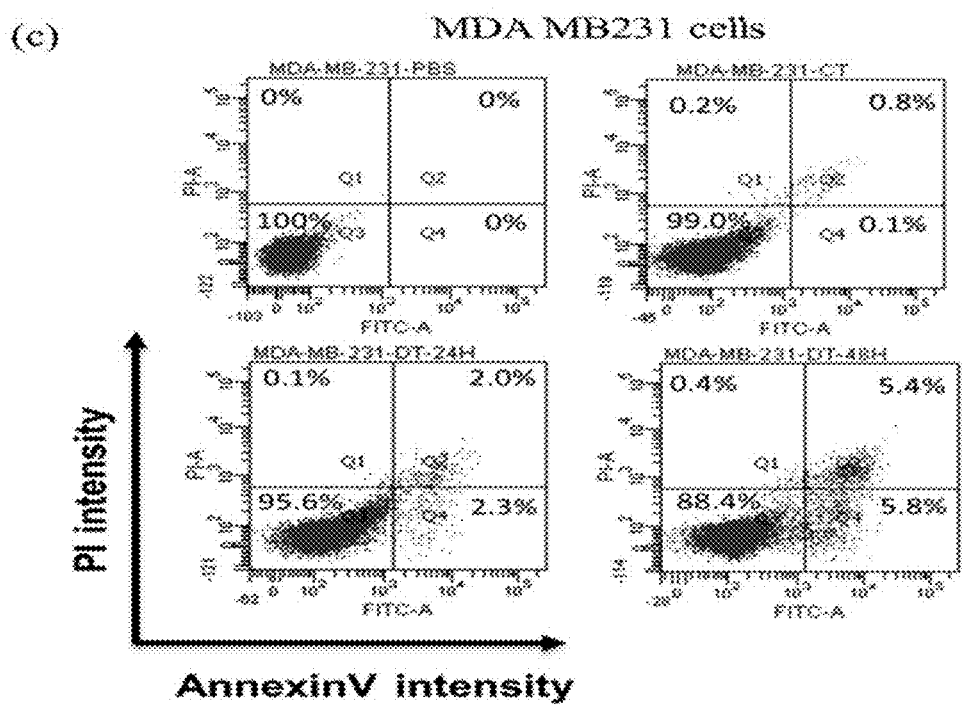

There is more early apoptosis, late apoptosis and necrosis in DT-treated prostate, lung and breast cancer cells compare to the PBS treated and CT treated cancer cells, in a time dependent manner (see Panels (a)-(c) of FIG. 6 for prostate cancer cells, Panels (a)-(b) of FIG. 7 for lung cancer and Panels (a)-(c) of FIG. 8 for breast cancer cells.

Example 7: The Effect of DT on Cell Damage and Cell Death Proteins

An in vitro evaluation on the damage effect of DT on cancer cells was performed, using prostate cancer cells (metastatic LNCaP and metastatic DU145, hormone therapy resistant and metastatic PC3 and 22RV1) and lung cancer cells (A549 and chemotherapy-resistant/metastatic H460).

Cancer cells were treated with a control vehicle, dihydrotestosterone (DHT), and various concentrations of DT between 6 to 24 hours. Cellular extracts of treated cancer cells were analyzed using Western Blot.

Figure 9:
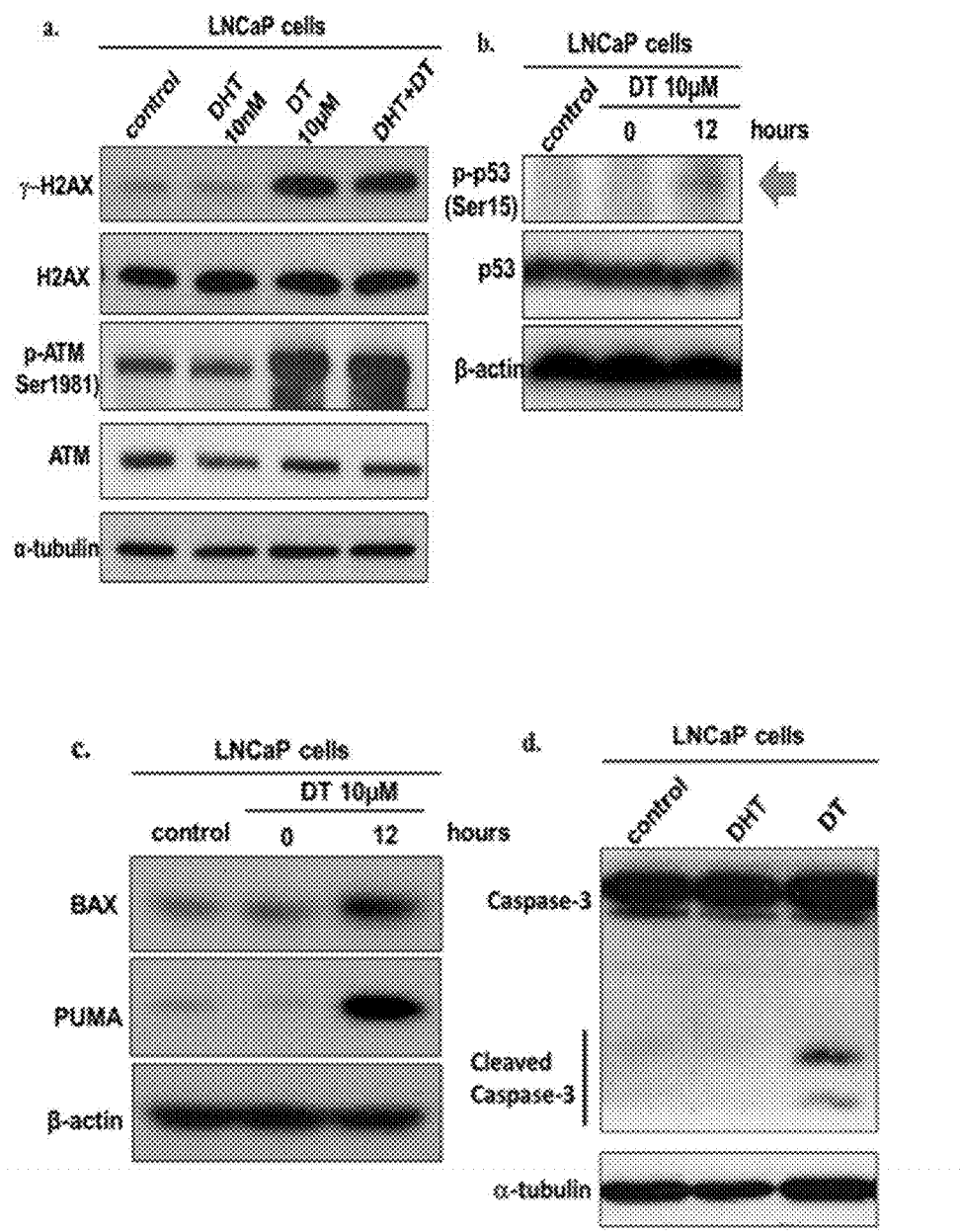
FIG. 9 is an assembly of western blot images, illustrating an embodiment of the compounds of formula (I) (DT) increased the DNA damage response proteins (γ-H2AX and phosphorylated-ATM), cell cycle regulatory protein (phosphorylated-p53) and program death proteins (PUMA, BAX, caspase-3, caspase-9 and PARP) in LNCaP (Panels a-d) and DU145 prostate cancer cells (Panels e-g).
Figure 9:
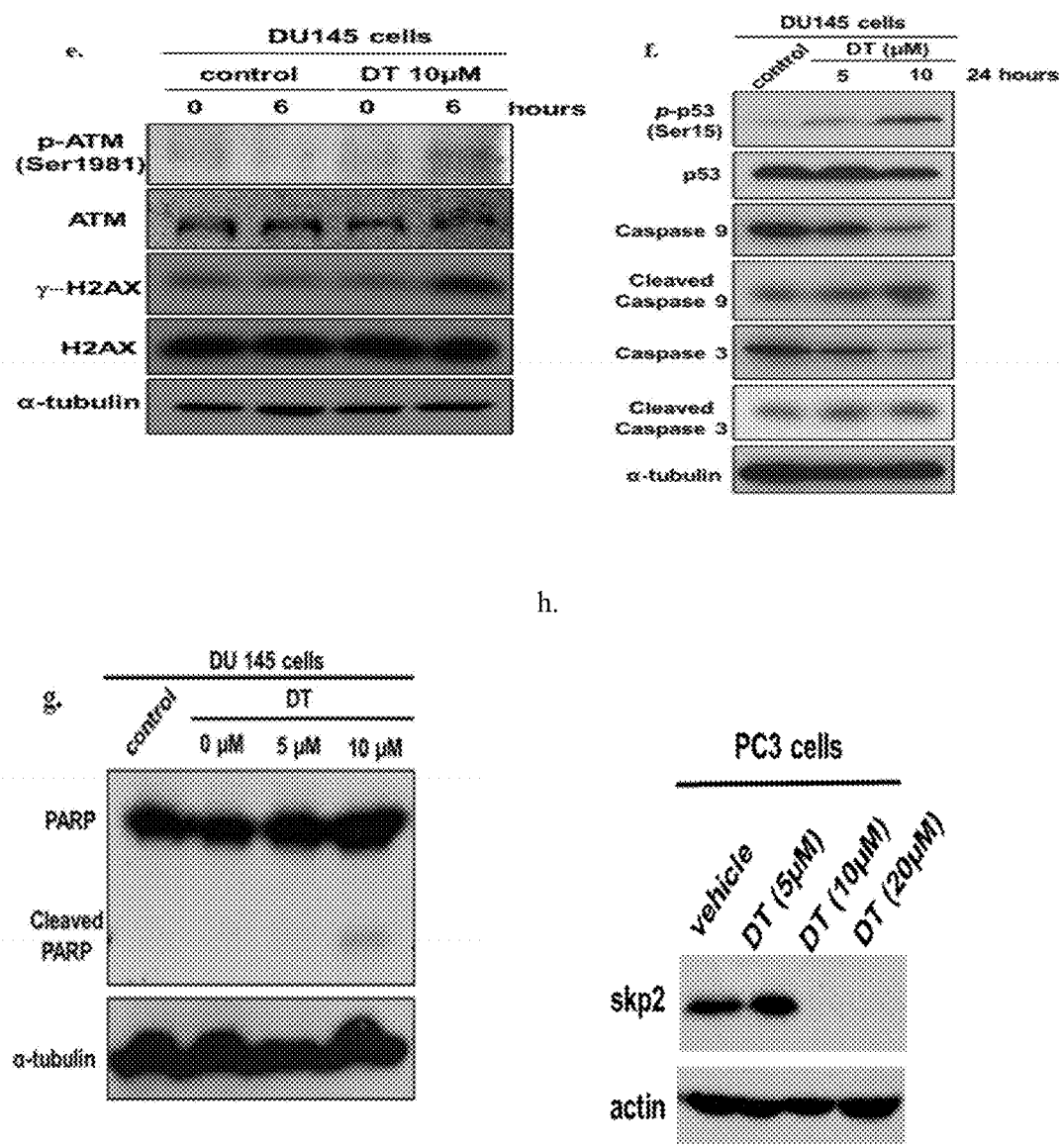
Figure 9:
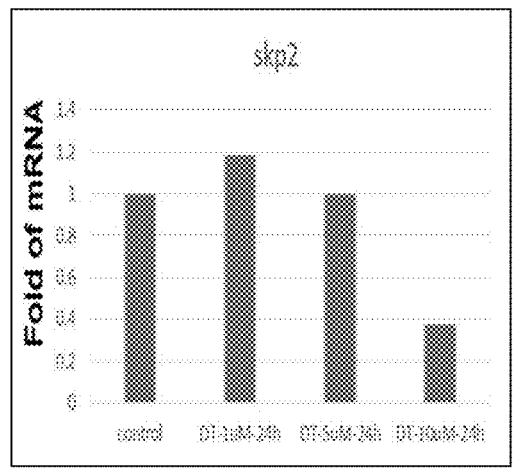
Figure 9:
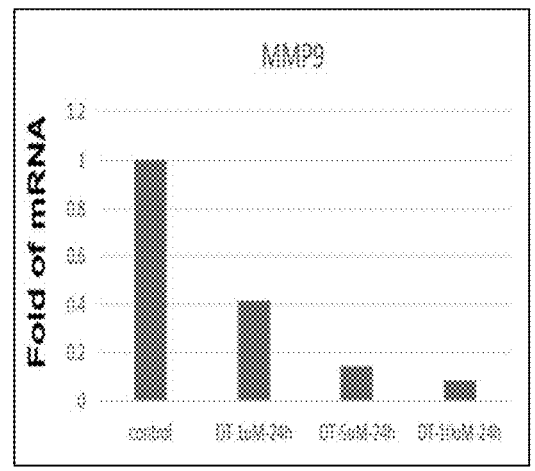
Figure 9:
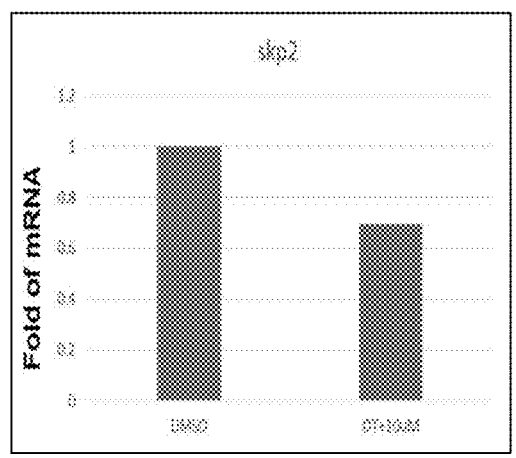
Figure 9:
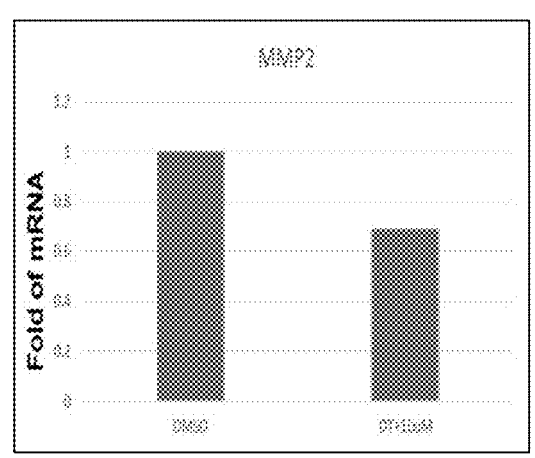

Panels (a)-(g) of FIG. 9 are western blot images illustrating an increase in DNA damage response proteins (γ-H2AX and phosphorylated-ATM), the cell cycle regulatory protein (phosphorylated-p53), cell program death proteins (PUMA, BAX, caspase-3, caspase-9 and PARP) in DT-treated prostate cancer cells, compared to control vehicle-treated prostate cancer cells, in a dose dependent and time dependent manner. α-tubulin was used as an internal loading control.

Figure 10:
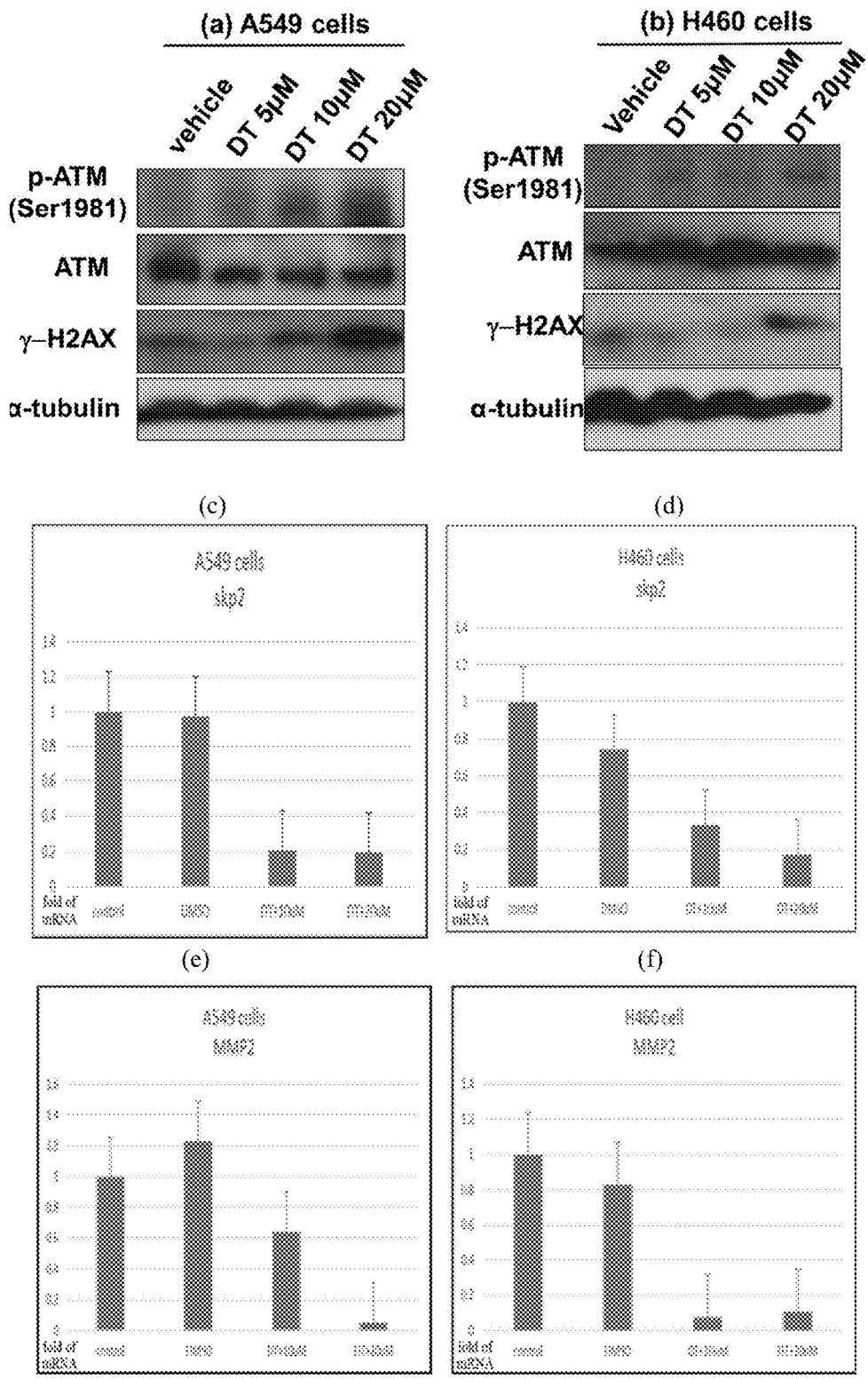
FIG. 10 is an assembly of western blot images, illustrating an embodiment of the compounds of formula (I) (DT) increased the DNA damage response proteins (γ-H2AX, phosphorylated-ATM) in A549 lung cancer cells (Panel (a)) and chemotherapy-resistant/metastatic H460 lung cancer cells (Panel (b)). Panels (c)-(j) are bar graphs illustrating DT reduces skps and its downstream genes, MMP2, MMP9 and E-cadherin, in A549 lung cancer cells (Panels (c) and (e)), chemotherapy-resistant/metastatic H460 lung cancer cells (Panels (d) and (f)), HTC116 colon cancer cells (Panels (g) and (i)) and tamoxifen resistant MCT7 breast cancer cells (Panels (h) and (j)).
Figure 10:
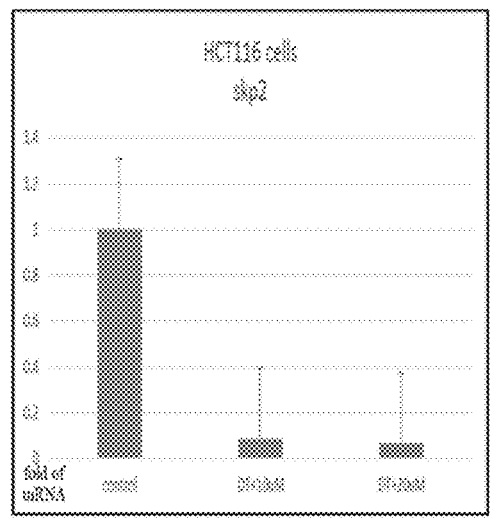
Figure 10:
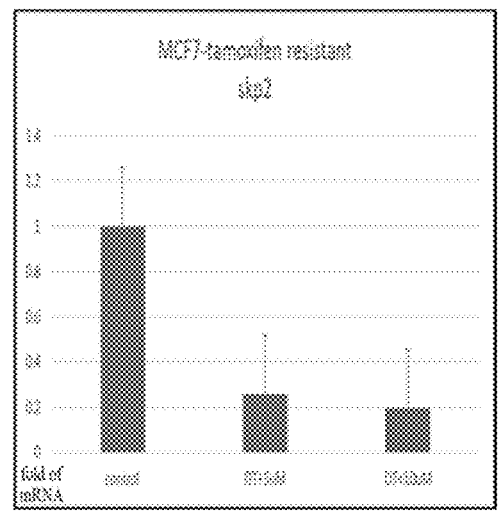
Figure 10:
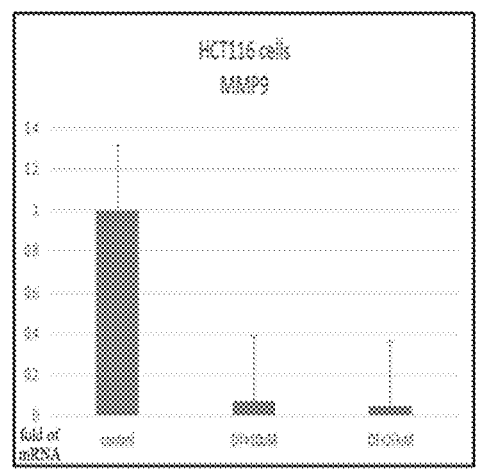
Figure 10:
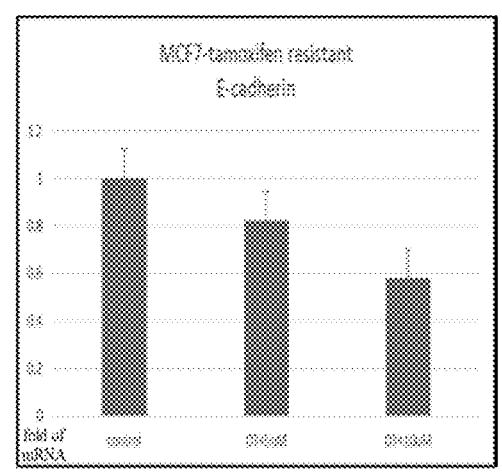

Panels (a)-(b) of FIG. 10 are western blot images illustrating an increase in DNA damage response proteins (γ-H2AX and phosphorylated-ATM) in DT-treated lung cancers, compare to control vehicle-treated lung cancer cells, in a dose dependent manner.

Example 8: The Effect of DT on skp2 and mRNA Level of its Downstream Genes

It has been reported that skp2 plays an important role in the metastasis of cancer cells. An in vitro evaluation of the effect of DT on prostate cancer cell metastasis was performed, by measuring the mRNA expression of skp2 in the following prostate cancer cell lines: meatstatic DU145 cells (Panels i-j of FIG. 9), hormone therapy resistant and metastatic PC3 cells (Panel h of FIG. 9), and 22RV1 cells (Panels k-l of FIG. 9), A549 lung cancer cells (Panels (c)-(e) of FIG. 10), chemotherapy-resistant/metastatic H460 lung cancer cells (Panels (d) and (f) of FIG. 10), HCT116 colon cancer cells (Panels (g) and (i) of FIG. 10) and MCF7-tamoxifen resistant breast cancer cells (Panels (h) and (j) of FIG. 10) using Western Blot analysis.

The cancer cells were treated with DMSO and various concentrations of DT. The results show that DT effectively inhibit mRNA expression of skp2 and its downstream genes, such as MMP2 or MMP9 or E-cadherin, in prostate cancer, lung cancer, colorectal cancer and target therapy resistant breast cancer. These results suggest that DT can block cancer cell invasion or metastasis via inhibiting skp2 pathway.

Example 9: The Effect of DT on Cancer Cell Invasion/Migration

An in vitro evaluation of the effect of DT on lung cancer cells (A549 and chemotherapy resistant/metastatic H460), prostate cancer cells (metastatic DU145) and colorectal cancer cells (chemotherapy resistant HCT116) invasion and migration was performed, using cell invasion assay and cell migration assay.

Cell migration is the movement of cells from one area to another generally in response to a chemical signal. Cell invasion is similar to cell migration, but requires a cell to migrate through an extracellular matrix or basement membrane extract by first enzymatically degrading that barrier and to then become established in a new location. Cell migration and/or cell invasion is critical to achieve metastasis of tumor.

Cell Invasion Assay: cells of interest were treated with a control vehicle, 5 or 10 µM of DT and incubated for 3 days. $1 \times 10^5$ cells were placed into the upper chamber of transwell plates (8 µm) with membranes pre-coated with 20% Matrigel and the bottom chamber contained 600 µL media supplemented with 10% fetal bovine serum (FBS). The cells migrated to the bottom of the chamber were fixed, stained and counted.

Cell Migration Assay: In vitro wound-healing assay was used to assess cell motility in two dimensions. Cancer cells were plated overnight to achieve a subconfluent cell layer in 24-well plates. A scratch was made on the cell layer with a micropipette tip, and cultures were washed twice with serum-free medium to remove floating cells. Cancer cells were incubated in a culture medium containing DT or the control vehicle. Wound healing was visualized by comparing photographs taken at the time of adding the DT/control vehicle and 24 h later. Three experiments were done in quadruplicates.

Figure 11:
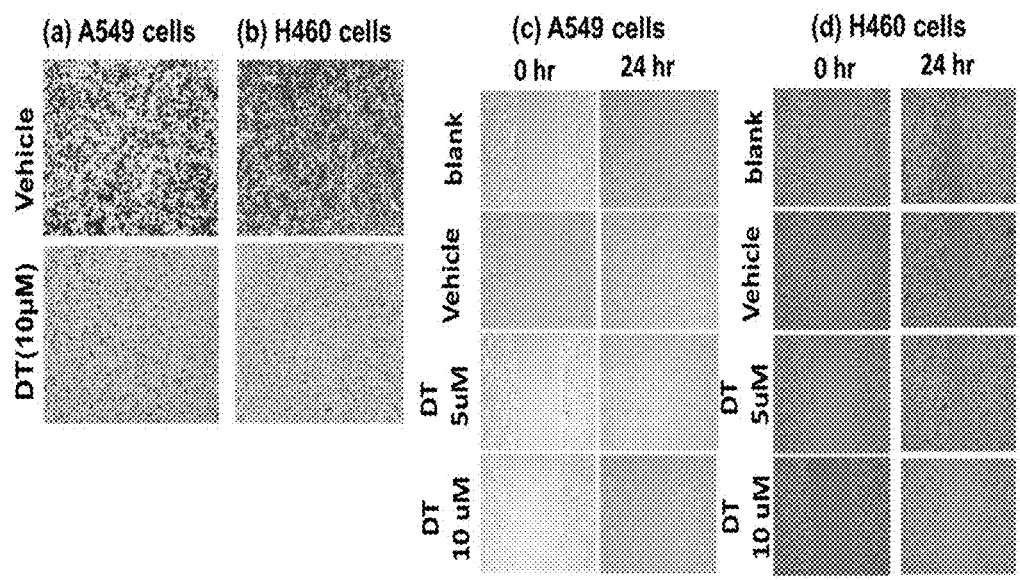
FIG. 11 is an assembly of microscopic images illustrating an embodiment of the compounds of formula (I) (DT) reduced the motility of lung cancer cells (Panels (a) and (b)) and reduced lung cancer cell migration into the wounded area compared to the control vehicle, in a dose dependent manner (Panels (c) and (d)).

Panel (a) of FIG. 11 illustrates DT reduced metastatic lung cancer cell motility and Panel (b) of FIG. 11 illustrates DT reduced metastatic lung cancer cell migration in a wound-induced migration assay, compared to the control vehicle, in a dose dependent fashion.

Figure 12:
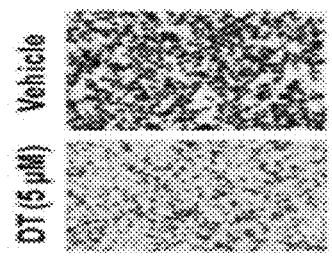
FIG. 12 is an assembly of microscopic images illustrating an embodiment of the compounds of formula (I) (DT) reduced the motility of prostate cancer cells (metastatic DU145—Panel (a), PC3—Panel (c) and 22RV1—Panel (e)) and reduced prostate cancer cell migration into the wounded area compared to the control vehicle (metastatic DU145—Panel (b), PC3—Panel (d), 22RV1—Panel (f)).
Figure 12:
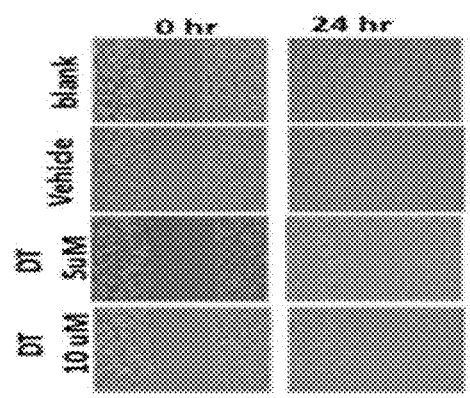
Figure 12:
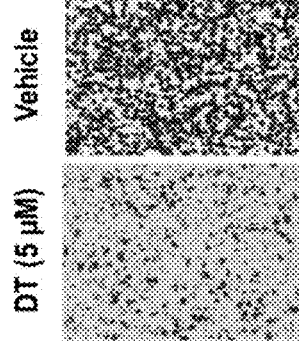
Figure 12:
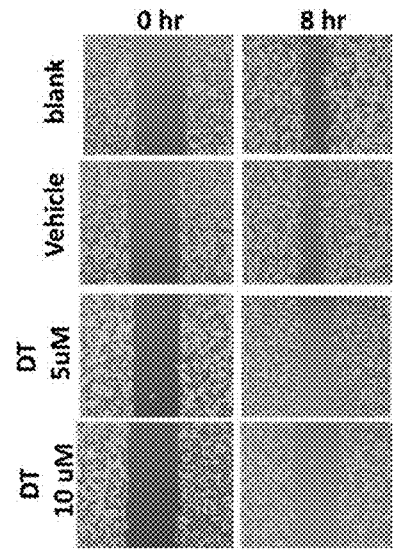
Figure 12:
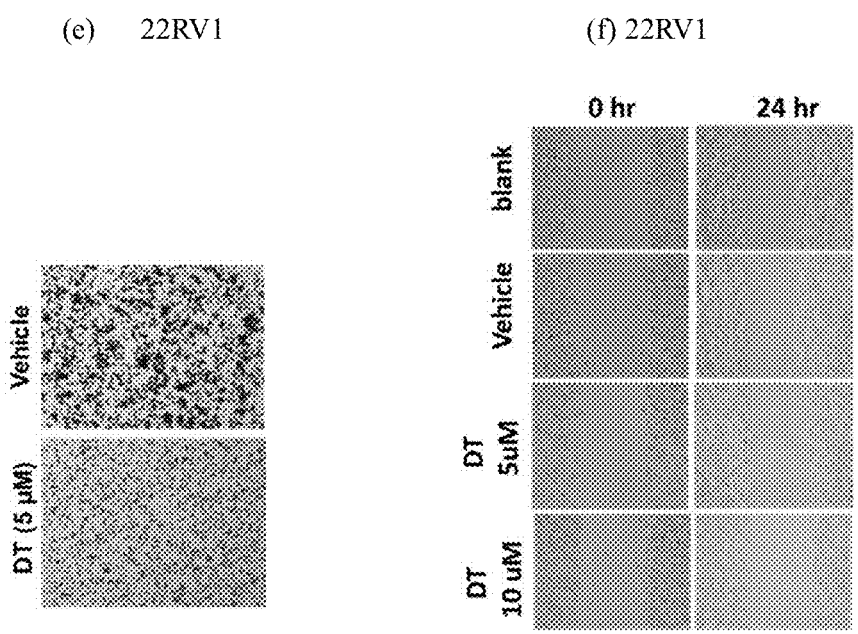

Panels (a)-(f) of FIG. 12 illustrate DT reduced the motility and migration of prostate cancer cells (metastatic DU145 cells—Panel (a) and (b), PC3 cells—Panels (c) and (d), and 22RV1 cells—Panels (e) and (f) in a wound-induced migration assay, compared to the control vehicle, in a dose dependent fashion.

Figure 13:
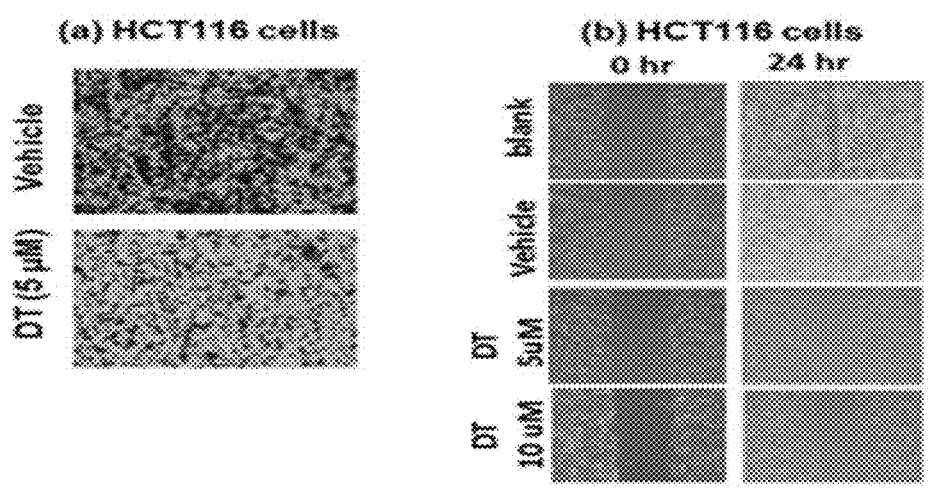
FIG. 13 is an assembly of microscopic images illustrating an embodiment of the compounds of formula (I) (DT) reduced the motility of colon cancer cells (Panel (a)) and reduced colon cancer cell migration into the wounded area compared to the control vehicle (Panel (b)).

Panel (a) of FIG. 13 illustrates DT reduced the motility of chemotherapy resistant colorectal cancer cells and Panel (b) of FIG. 13 illustrates DT reduced chemotherapy resistant colorectal cancer cell migration in a wound-induced migration assay, compared to the control vehicle, in a dose dependent fashion.

These results suggest DT is effective in reducing cancer metastasis, including metastatic cancer cells.

Example 10: The Effect of DT on the Expression of CCL2 in Macrophages and Prostate Cancer Cells It has been reported that increased CCL2 expression enhances cancer cell metastasis via macrophage recruitment. The effect of DT on CCL2 expression in RAW264.7 macrophages, THP1 monocytes and prostate cancer cells (metastatic DU145 and hormone therapy resistant and metastatic PC3) was examined by treating the cells with DMSO (control), 5 or 10 µM DT for 24 hours.

The culture medium was collected and the concentration of CCL2 was measured using ELISA assay.

Figure 14:
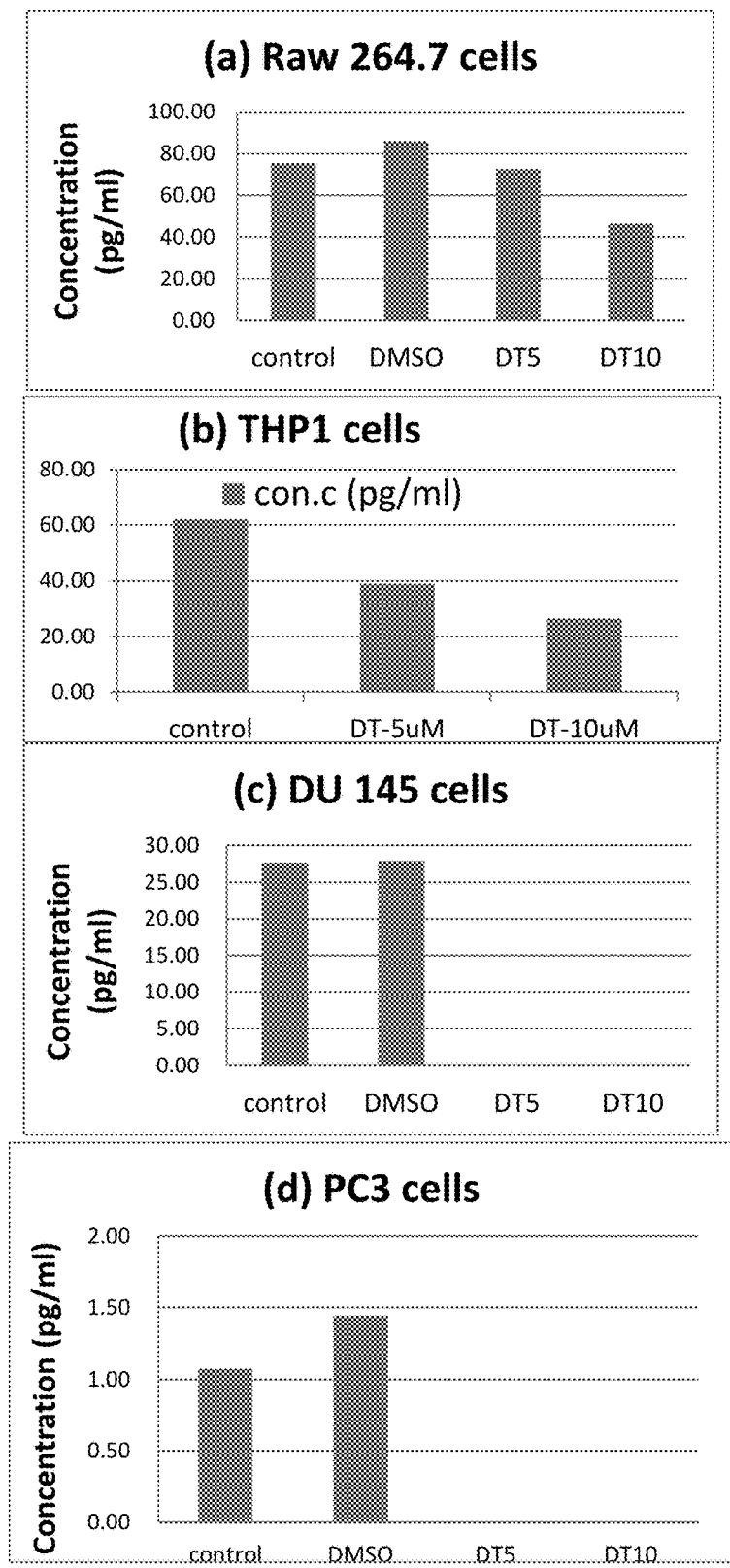
FIG. 14 is an assembly of bar graphs showing the effect of an embodiment of the compounds of formula (I) (DT) on the expression of CCL2 in Raw264.7 macrophage (Panel (a)), THP1 monocyte (Panel (b)), DU145 metastatic prostate cancer cells (Panel (d)) and PC3 prostate cancer cells (Panel (d)).

The results show DT effectively inhibit the production of CCL2 in macrophages (Panel (a) of FIG. 14), Panel (b) of FIG. 14), metastatic DU145 prostate cancer cells (Panel (c) of FIG. 14) and hormone therapy resistant and metastatic PC3 prostate cancer cells (Panel (d) of FIG. 14).

Example 11: The Effect of DT on Prostate Cancer Cell Invasion in DT-Treated Monocyte/Cancer Cell Co-Culture and DT-Treated Macrophage/Cancer Cell Co-Culture As illustrated in Example 10, the production of CCL2 was inhibited by DT in both prostate cancer cells and macrophage, the effect of DT on monocyte/cancer cell co-culture and macrophage/cancer cell co-culture was examined using the invasion assay described in Example 9.
  (a) THP1 monocytes, Raw264.7 macrophage, monocyte/prostate cancer co-culture and macrophage/prostate cancer co-culture were treated with a vehicle (DMSO), 5 or 10 µM DT for 24 hours, the cultured medium was collected and placed into the lower chamber of a transwell plate.
  (b) Prostate cancer cells (PC3, DU145 and 22RV1) were placed in the cell invasion assay). The level of CCL2 in the invasion assay was measured by ELIZA method.

Figure 15:
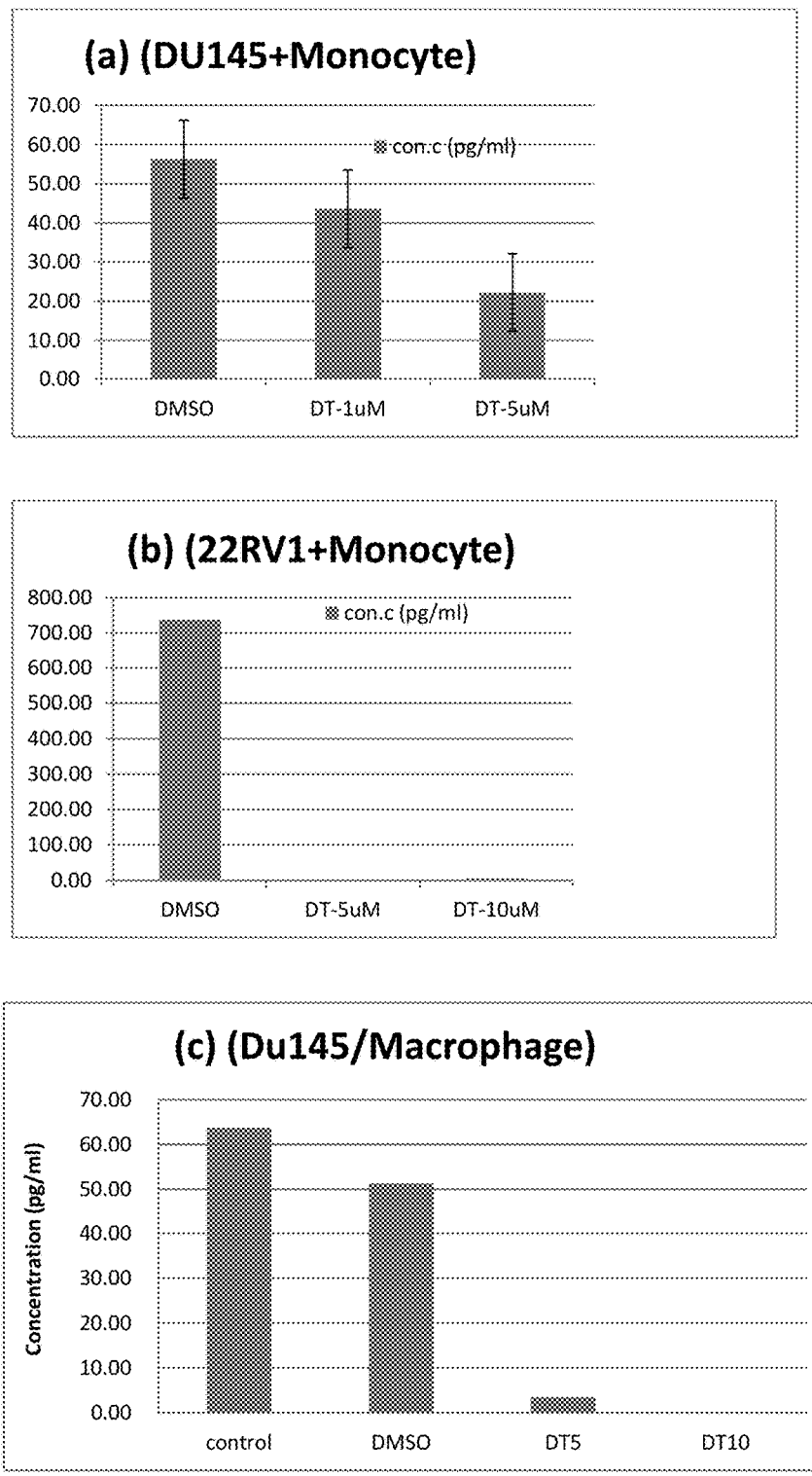
FIG. 15 is an assembly of bar graphs showing the effect of an embodiment of the compounds of formula (I) (DT) on the expression of CCL2 in THP1/DU145 co-culture (Panel (a)), THP1 cells/22RV1 co-culture (Panel (b)) and RAW 264.7 cells/DU145 co-culture (Panel (c)).

The results show that 5-10 µM of DT significantly inhibit the migration of prostate cancer cells in a dose-dependent manner in the DT-treated monocyte medium, DT-treated macrophage medium, DT-treated monocyte/prostate cancer co-culture medium and DT-treated macrophage/prostate cancer co-culture medium (results not shown). The concentration of CCL2 was significantly reduced in DT-treated monocyte/DU145 co-culture medium (Panel (a) of FIG. 15, DT-treated monocyte/22RV1 co-culture medium (Panel (b) of FIG. 15 and DT-treated macrophage/DU145 co-culture medium (Panel (c) of FIG. 15.

Example 11: The Effect of DT on the Macrophages and Prostate Cancer Cells Migration An in vitro study to evaluate the effect of DT on macrophage and cancer cell migration was performed.

Macrophages were treated with a vehicle (DMSO), 5 or 10 µM DT. The mobility of the macrophages was not affected by DT. The macrophages were placed in an invasive assay, prepared accordingly to the steps in Example 10 using DT-treated prostate cancer cells (DU145 or PC3) incubated in 10% CD-FBS RPMI medium.

The results show untreated prostate cancer cells (DU145 and PC3) induce macrophage migration, whereas DT-treated prostate cancer cells inhibit macrophage migration, which is known to promote tumor invasion and metastasis (microscopic images not shown).

What is claimed is:
1. A method for inhibiting cancer cells, comprising:
    administering to a subject in need thereof a therapeutically effective amount of a compound of formula (I),

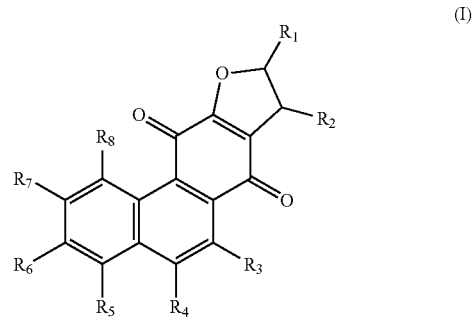

or a pharmaceutically acceptable salt thereof,
wherein:

R$_1$ to R$_8$ are each independently H, a hydroxyl group, a nitro group, an amino group, a halogen, a substituted or unsubstituted C$_1$-C$_{10}$ alkyl group, and a substituted or unsubstituted C$_1$-C$_{10}$ alkoxy group, wherein the C$_1$-C$_{10}$ alkyl group or the C$_1$-C$_{10}$ alkoxy group may be substituted by at least one selected from the group consisting of a hydroxyl group, a nitro group, an amino group, a halogen, a substituted or unsubstituted C$_1$-C$_{10}$ alkyl group, and a substituted or unsubstituted C$_1$-C$_{10}$ alkoxy group, wherein the cancer cells are selected from the group consisting of prostate cancer, endometrial cancer, breast cancer and colorectal cancer.

2. The method according to claim 1, wherein R$_2$ and R$_5$ are each a substituted or unsubstituted C$_1$-C$_{10}$ alkyl group, and R$_1$, R$_3$, R$_4$, R$_6$, R$_7$, and R$_8$ are each H.

3. The method according to claim 1, wherein R$_2$ and R$_5$ are each a methyl group, and R$_1$, R$_3$, R$_4$, R$_6$, R$_7$, and R$_8$ are each H.

4. The method according to claim 1, wherein the cancer cells are cancer therapy resistant.

5. The method according to claim 4, wherein the therapy resistant cancer cells are selected from the group consisting of breast cancer, prostate cancer and colorectal cancer.

6. The method according to claim 4, wherein the cancer cells are chemotherapy resistant.

7. The method according to claim 4, wherein the cancer cells are target therapy resistant.

8. A method for reducing cancer metastasis, comprising:

administering to a subject in need thereof a therapeutically effective amount of a compound of formula (I),

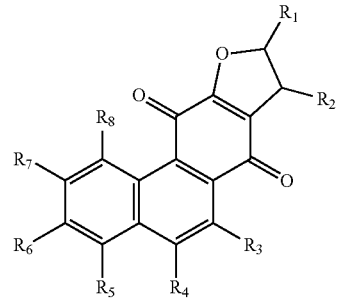

or a pharmaceutically acceptable salt thereof,
wherein:

R$_1$ to R$_8$ are each independently H, a hydroxyl group, a nitro group, an amino group, a halogen, a substituted or unsubstituted C$_1$-C$_{10}$ alkyl group, and a substituted or unsubstituted C$_1$-C$_{10}$ alkoxy group, wherein the C$_1$-C$_{10}$ alkyl group or the C$_1$-C$_{10}$ alkoxy group may be substituted by at least one selected from the group consisting of a hydroxyl group, a nitro group, an amino group, a halogen, a substituted or unsubstituted C$_1$-C$_{10}$ alkyl group, and a substituted or unsubstituted C$_1$-C$_{10}$ alkoxy group, wherein the cancer cells are selected from the group consisting of prostate cancer, endometrial cancer, breast cancer and colorectal cancer.

9. The method according to claim 8, wherein R$_2$ and R$_5$ are each a substituted or unsubstituted C$_1$-C$_{10}$ alkyl group, and R$_1$, R$_3$, R$_4$, R$_6$, R$_7$, and R$_3$ are each H.

10. The method according to claim 8, wherein R$_2$ and R$_5$ are each a methyl group, and R$_1$, R$_3$, R$_4$, R$_6$, R$_7$, and R$_8$ are each H.

* * * * *